(12) United States Patent
Uchiyama et al.

(10) Patent No.: US 9,002,434 B2
(45) Date of Patent: Apr. 7, 2015

(54) MEDICAL DEVICE POSITION DETECTING SYSTEM, MEDICAL DEVICE GUIDING SYSTEM, AND POSITION DETECTING METHOD FOR MEDICAL DEVICE

(75) Inventors: Akio Uchiyama, Yokohama (JP); Atsushi Kimura, Akiruno (JP); Ryoji Sato, Hino (JP); Atsushi Chiba, Hachioji (JP)

(73) Assignee: Olympus Corporation (JP)

( * ) Notice: Subject to any disclaimer, the term of this patent is extended or adjusted under 35 U.S.C. 154(b) by 1706 days.

(21) Appl. No.: 12/095,341

(22) PCT Filed: Dec. 4, 2006

(86) PCT No.: PCT/JP2006/324191
§ 371 (c)(1),
(2), (4) Date: May 29, 2008

(87) PCT Pub. No.: WO2007/064013
PCT Pub. Date: Jun. 7, 2007

(65) Prior Publication Data
US 2009/0171190 A1  Jul. 2, 2009

(30) Foreign Application Priority Data

Dec. 2, 2005  (JP) ................................. 2005-349178

(51) Int. Cl.
*A61B 5/05* (2006.01)
*G08B 21/00* (2006.01)
*A61B 5/06* (2006.01)
*A61B 1/00* (2006.01)
*A61B 1/04* (2006.01)
*A61B 19/00* (2006.01)
*A61B 5/00* (2006.01)

(52) U.S. Cl.
CPC ............... *A61B 5/06* (2013.01); *A61B 1/00158* (2013.01); *A61B 1/041* (2013.01); *A61B 2019/2261* (2013.01); *A61B 5/7232* (2013.01)

(58) Field of Classification Search
USPC .................. 600/407, 410, 424, 420; 324/301; 340/686.1
See application file for complete search history.

(56) References Cited

U.S. PATENT DOCUMENTS 7,123,129 B1 * 10/2006 Schrott et al. ................ 340/10.1
2005/0216231 A1 * 9/2005 Aoki et al. .................... 702/183

FOREIGN PATENT DOCUMENTS

JP  H09-28661 A  2/1997
JP  2003-245243 A  9/2003
(Continued)

OTHER PUBLICATIONS

International Search Report dated Feb. 20, 2007 issued in corresponding PCT Application No. PCT/JP2006/324191.

*Primary Examiner* — Katherine Fernandez
(74) *Attorney, Agent, or Firm* — Ostrolenk Faber LLP

(57) ABSTRACT

Position detection of a medical device is prevented from being impossible even when the frequency characteristic of a magnetic induction coil is varied in accordance with the state of an external magnetic field for guiding the medical device. A medical device position detecting system is a medical device position detecting system which is inserted into the body of a subject and guided by an external magnetic field, and it is equipped with a resonance circuit that is mounted in the medical device, contains a magnetic induction coil having a magnetic material inside and generates an alternate magnetic field, an alternate magnetic field detecting device that is disposed at the outside of an operation region of the medical device and detects the alternate magnetic field generated by the magnetic induction coil, a position information calculator for calculating position information of the medical device on the basis of the detected alternate magnetic field, and a frequency setting unit for setting at least one of the frequency of the alternate magnetic field detected by the alternate magnetic field detecting device and the frequency of the alternate magnetic field generated by the magnetic induction coil on the basis of at least one of the intensity and direction of an external magnetic field at the position of the magnetic induction coil.

31 Claims, 26 Drawing Sheets

(56) References Cited

FOREIGN PATENT DOCUMENTS

| | | | |
|---|---|---|---|
| JP | 2004-255174 A | 9/2004 | |
| JP | 2005-121573 A | 5/2005 | |
| JP | 2005-304638 A | 11/2005 | |
| WO | WO 2004/014225 | 2/2004 | |
| WO | WO 2006/064972 | * | 6/2006 |

* cited by examiner

MEDICAL DEVICE POSITION DETECTING SYSTEM, MEDICAL DEVICE GUIDING SYSTEM, AND POSITION DETECTING METHOD FOR MEDICAL DEVICE

CROSS REFERENCE TO RELATED APPLICATION

The present application is a 35 U.S.C. §§371 national phase conversion of PCT/JP2006/324191, filed Dec. 4, 2006, which claims priority of Japanese Application No. 2005-349178, filed Dec. 2, 2005, the disclosures of which have been incorporated herein by reference. The PCT International Application was published in the Japanese language.

TECHNICAL FIELD

The present invention relates to a medical device position detecting system, a medical device guiding system, and a position detecting method for a medical device.

BACKGROUND ART

A medical device represented by a swallow type capsule endoscope or the like which is administered into an object under test such as a subject or the like and passed through a coelomoduct to obtain images in the coelomoduct at a target position has been recently studied and developed for the purpose of its practical use. The medical device such as the capsule endoscope or the like is equipped with an image pickup element such as CCD (Charge Coupled Device) or the like which can perform the above medical action, for example, obtain an image, and obtain an image at a target site in the coelomoduct.

It is necessary that the capsule endoscope is controlled to be guided irrespective of peristalsis of the coelomoduct so that the capsule endoscope is made to surely reach a target site in the coelomoduct or stay at a target site to be subjected to detailed examination or the like which needs time. In order to guide the capsule endoscope, it is required to detect a place at which the capsule endoscope is located in the coelomoduct, and there has been proposed a technique of detecting the position of the capsule endoscope guided to a place (the inside of a coelomoduct or the like) which cannot be visually checked (for example, see Patent Citation 1). Furthermore, a method of detecting the position and direction of a wireless magnetic marker is disclosed in Patent Citation 2.

The Patent Citation 1 discloses a technique that electromagnetism occurring from a capsule endoscope having a magnetic field generating field in which an LC resonance circuit is connected to an alternate power source is detected by plural external detection devices to detect the position of the capsule endoscope.

Furthermore, the Patent Citation 2 discloses a resonance circuit containing a magnetic induction coil having a magnetic core as a wireless magnetic marker. According to the method of the Patent Citation 2, the position and direction of the wireless magnetic maker can be detected by utilizing the fact that a given external magnetic field is varied due to existence of a resonance circuit having a magnetic induction coil containing a wireless magnetic marker therein.

Patent Citation 1: PCT International Publication No. WO2004/014225 A1 Pamphlet
Patent Citation 2: Japanese Unexamined Patent Application, Publication No. 2005-121573

DISCLOSURE OF INVENTION

However, when the medical device is guided by using the external magnetic field, there is a disadvantage that the characteristic of the magnetic induction coil for position detection which is disposed in the medical device is varied in accordance with the state of the external magnetic field. As a result, there is a disadvantage that the position detection precision of the medical device is rapidly lowered, and it makes it difficult to guide the medical device to an accurate direction.

The present invention has been implemented in view of the foregoing situation, and has an object to provide a position detection system and a position detecting method for a medical device such as a capsule endoscope or the like by which the position detection of the medical device can be prevented from being made impossible even when the frequency characteristic of a magnetic induction coil used for the position detection of the medical device is varied in accordance with the state of an external magnetic field for guiding the medical device. Furthermore, the present invention has another object to provide a medical device guiding system that can guide the medical device precisely even when the frequency characteristic of the magnetic induction coil is varied in accordance with the state of the external magnetic field for guiding the medical field.

In order to attain the above object, the present invention provides the following means.

According to a first aspect of the present invention, there is provided a medical device position detecting system which is introduced into the body of a subject and guided by an external magnetic field comprises: a resonance circuit that is mounted in the medical device and contains a magnetic induction coil having a magnetic core to be able to generate an alternate magnetic field; an alternate magnetic field detecting device that is disposed at the outside of an operation region of the medical device and detects the alternate magnetic field generated by the magnetic induction coil; a position information calculator for calculating position information of the medical device on the basis of the alternate magnetic field detected by the alternate magnetic field detecting device; an external magnetic field information calculator for calculating the intensity of the external magnetic field at the position of the medical device on the basis of the position information calculated by the position information calculator; and a frequency setting unit for setting the frequency of the alternate magnetic field detected by the alternate magnetic field detecting device on the basis of the intensity of the external magnetic field calculated by the external magnetic field information calculator.

According to this aspect, when the medical device is introduced into the body of a subject and is guided by an external magnetic field, and an alternate magnetic field is generated by actuating a magnetic induction coil of a resonance circuit provided in the medical device, the alternate magnetic field is detected by the alternate magnetic field detecting device disposed at the outside of the operation region of the medical device. When the alternate magnetic field is detected, the position detection of the medical device is carried out by operating the position information calculator. Furthermore, the intensity of the external magnetic field at the position of the medical position is calculated by operating the external magnetic field information calculator, and the frequency of the alternate magnetic field detected by the alternate magnetic field detecting device is set on the basis of the intensity of the external magnetic field by operating the frequency setting unit.

When the intensity of the external magnetic field acting on the magnetic induction coil varies, the frequency characteristic of the magnetic induction coil varies. Therefore, if the frequency of the alternate magnetic field detected by the alternate magnetic field detecting device is fixed, the detection sensitivity of the alternate magnetic field is rapidly lowered, so that the precision of the position information of the medical device which is calculated by the position information calculator is lowered. According to the present invention, the frequency of the alternate magnetic field detected by the alternate magnetic field detecting device is set by operating the frequency setting unit in conformity with this variation of the intensity of the external magnetic field, so that the proper frequency of the alternate magnetic field can be set in conformity with the intensity of the external magnetic field and thus the medical device can be prevented from falling into a guide-impossible state due to the rapid reduction in the position detection precision.

In the above aspect, there may be provided an alternate magnetic field generating device for generating the alternate magnetic field in the neighborhood of the frequency set by the frequency setting unit at the position of the magnetic induction coil.

In this case, the frequency of the alternate magnetic field generated by the magnetic induction coil and the frequency of the alternate magnetic field detected by the alternate magnetic field detecting device can be made substantially coincident with each other, whereby the detection sensitivity can be enhanced.

In the above aspect, it is preferable that the resonance circuit is operated in the neighborhood of the frequency set by the frequency setting unit.

In addition to the case where the alternate magnetic field is supplied to the position of the magnetic induction coil and a large alternate magnetic field is generated by the resonance of the resonance circuit containing the magnetic induction coil, the frequency of the alternate magnetic field generated by the magnetic induction coil and the frequency of the alternate magnetic field detected by the alternate magnetic field detecting device can be likewise made substantially coincident with each other by operating the resonance circuit itself at the set frequency.

In the above aspect, the resonance circuit may constitute a self-excited oscillation circuit.

With this construction, the resonance circuit generates an alternate magnetic field of a resonance frequency determined by elements constituting the resonance circuit concerned, and the resonance frequency concerned is varied in accordance with the state of an external magnetic field. However, the frequency of the alternate magnetic field detected by the alternate magnetic field detecting device is set by the frequency setting unit, so that the medical device can be prevented from falling into the guide-impossible state due to the rapid reduction of the position detection precision.

Furthermore, in the above aspect, the frequency setting unit may be equipped with a storage unit for storing the intensity of the external magnetic field occurring at the position of the medical device and the detected frequency while associating the intensity of the external magnetic field and the detected frequency with each other, and set the frequency of the alternate magnetic field detected by the alternate magnetic field detecting device to a detection frequency selected from the storage unit on the basis of the intensity of the external magnetic field.

With this construction, the detection frequency corresponding to the external magnetic field is read out from the storage and the alternate magnetic field is detected rapidly with high sensitivity, thereby preventing the rapid reduction of the position detection precision.

Still furthermore, in the above aspect, the position information calculated by the position information calculator contains the position and direction of the medical device, there is provided a magnetic field angle calculator for calculating a magnetic field angle as the intersection angle between the direction of an external magnetic field and the direction of an alternate magnetic field generated by the magnetic induction coil on the basis of the direction of the external magnetic field at the position of the medical device and the direction of the medical device, and the frequency setting unit is having a storage unit for storing the magnetic field angle and the detection frequency while associating the magnetic field angle and the detection frequency with each other and sets the frequency of the alternate magnetic field detected by the alternate magnetic field detecting device to a detection frequency selected from the storage unit on the basis of the magnetic field angle.

With this construction, the magnetic angle corresponding to the intersection angle between the direction of the external magnetic field and the direction of the alternate magnetic field generated by the magnetic induction coil can be calculated by operating the magnetic angle calculator.

When the magnetic angle varies, the frequency characteristic of the magnetic induction coil varies. Therefore, if the frequency of the alternate magnetic field detected by the alternate magnetic field detecting device is fixed, the detection sensitivity of the alternate magnetic field would be rapidly lowered, so that the precision of the position information of the medical device calculated by the position information calculator is reduced. According to this aspect, when the magnetic angle varies, the frequency of the alternate magnetic field detected by the alternate magnetic field detecting device is set to a pre-stored detection frequency in conformity with the variation of the magnetic field angle by operating the frequency setting unit, so that the alternate magnetic field can be detected rapidly with high sensitivity in conformity with the magnetic field angle, and thus the medical device can be prevented from falling into the guide-impossible state due to the rapid reduction of the position detection precision.

In the above aspect, the medical device may be any one of a capsule medical device, a catheter and an endoscope device.

In the above aspect, the medical device may contain a magnet for guiding the medical device by an external magnetic field, and the frequency setting unit may set the frequency of the alternate magnetic field detected by the alternate magnetic field detecting device on the basis of the composite magnetic field between a magnetic field generated at the position of the magnetic induction coil by the magnet and an external magnetic field generated at the position of the magnetic induction coil by the magnetic field generating device.

With this construction, the external magnetic field can be made to act on the magnet to thereby guide the medical device containing the magnet. In this case, both the external magnetic field and the magnetic field based on the magnet are applied to the magnetic induction coil, and the frequency of the alternate magnetic field acting on the magnetic induction coil is set on the basis of the composite magnetic field of these magnetic fields, so that the frequency of the alternate magnetic field can be set more properly.

According to a second aspect of the present invention, a medical device guiding system comprises the above position detecting system, a magnetic generating device that is disposed at the outside of the operation region of the medical device, and generates an external magnetic field acting on the magnet in the medical device, and a magnetic field control device for controlling the external magnetic field applied to the magnet by the magnetic field generating device.

According to this aspect, the external magnetic field is generated at the position of the medical device by the operation of the magnetic field generating device, and the magnetic field acts on the magnet in the medical device, whereby the medical device is guided according to the external magnetic field. The magnetic field generating device is controlled by the magnetic field control device, so that the medical device is guided according to the direction of the external magnetic field controlled by the magnetic field control device. In this case, even when the resonance frequency of the resonance circuit in the medical device varies in accordance with the state of the external magnetic field occurring at the position of the medical device, the detection frequency of the alternate magnetic field by the alternate magnetic field detecting device can be properly set by the operation of the position detecting system, so that the medical device can be guided to desired position and direction without lowering the detection precision of the position information of the medical device.

In the above embodiment, the magnetic field control device may control the magnetic field generating device to rotate the direction of the external magnetic field.

With this construction, the external magnetic field is applied as a rotational magnetic field to the medical device by the magnetic field control device, thereby rotating the medical device.

Furthermore, in the above aspect, the medical device may be equipped with a slender insertion unit and a spiral mechanism that is disposed on the outer peripheral surface of the insertion unit and converting a rotational motion around a longitudinal axis to a propelling motion in the longitudinal axis direction, and the magnet may be disposed so that the magnetic poles thereof are oriented in a direction perpendicular to the longitudinal axis.

With this construction, the medical device is rotated around the longitudinal axis by the action of the rotational magnetic field formed around the longitudinal axis, and the rotational motion of the medical device is converted to the propelling motion by the action of the spiral mechanism, whereby the medical device can be guided in the longitudinal direction.

Still furthermore, in the above aspect, the magnetic field control device may control to stop the external magnetic field when the intersection angle between the direction of the medical device and the direction of the external magnetic field is smaller than a predetermined angle.

When the intersection angle between the direction of the medical device and the direction of the external magnetic field is smaller than the predetermined angle, it is difficult to rotate the medical device around the longitudinal axis by the external magnetic field, so that unstable guidance of the medical device can be prevented by stopping the external magnetic field. Furthermore, when the intersection angle between the direction of the medical device and the direction of the external magnetic field is smaller than the predetermined angle, the frequency characteristic of the magnetic induction coil varies greatly. Therefore, by temporarily stopping the external magnetic field, the position and direction of the medical device can be more accurately detected, and thus it can be restored to more stable guidance.

Still furthermore, in the above aspect, the magnetic field generating device may generate an external magnetic field in any direction, the medical device may be equipped with a slender insertion portion, and the magnet may be disposed so that the magnetic poles are oriented in a direction along the longitudinal axis of the insertion portion.

With this construction, the medical device can be controlled so that it is oriented in the direction of the external magnetic field, and in this case, unstable guidance due to rapid reduction of the position detection precision can be prevented.

In the above aspect, the magnetic field generating device may generate a gradient magnetic field.

In the magnetic induction coil disposed in the gradient magnetic field, the intensity of the external magnetic field is varied in accordance with the disposing position of the magnetic induction coil, so that the frequency characteristic varies in accordance with the intensity of the external magnetic field. According to the present invention, the detection frequency of the alternate magnetic field can be properly set in accordance with the intensity of the external magnetic field, so that the reduction of the detection precision of the position information of the medical device can be prevented.

A third aspect of the present invention is a position detecting method for detecting the position of a medical device when an external magnetic field is applied to the medical device, the medical device being introduced into the body of a subject and being equipped with a resonance circuit containing a magnetic induction coil having a magnetic core for generating an alternate magnetic field signal and with a magnet for guidance, the position detecting method comprising: detecting an alternate magnetic field at the outside of an operation region of the medical device generated by the magnetic induction coil; calculating position information of the medical device on the basis of the detected alternate magnetic field; calculating the intensity of an external magnetic field at the position of the medical device on the basis of the calculated position information; and setting the frequency of the alternate magnetic field to be detected on the basis of the calculated intensity of the external magnetic field.

When the intensity of the external magnetic field acting on the magnetic induction coil varies, the frequency characteristic of the magnetic induction coil varies. Therefore, if the frequency of the detected alternate magnetic field is fixed, the detection sensitivity of the alternate magnetic field would be rapidly lowered, so that the precision of the calculated position information of the medical device is lowered. According to the present invention, when the intensity of the external magnetic field varies, the frequency of the detected alternate magnetic field is set in conformity with the variation of the intensity of the external magnetic field. Therefore, the frequency of the alternate magnetic field can be set properly in conformity with the intensity of the external magnetic field, so that the medical device can be prevented from falling into a guide-impossible state due to the rapid reduction of the position detection precision.

According to the medical device position detecting system, the medical device guiding system and the medical device position detecting method according to the present invention, even when the frequency characteristic of the magnetic induction coil for position detection in the medical device varies in accordance with the condition of the external magnetic field, the frequency for position detection at the outside of the operation region of the medical device is changed in conformity with the variation of the frequency characteristic, so that the accurate position information can be detected without lowering the detection precision.

EXPLANATION OF REFERENCE

Figure 1:
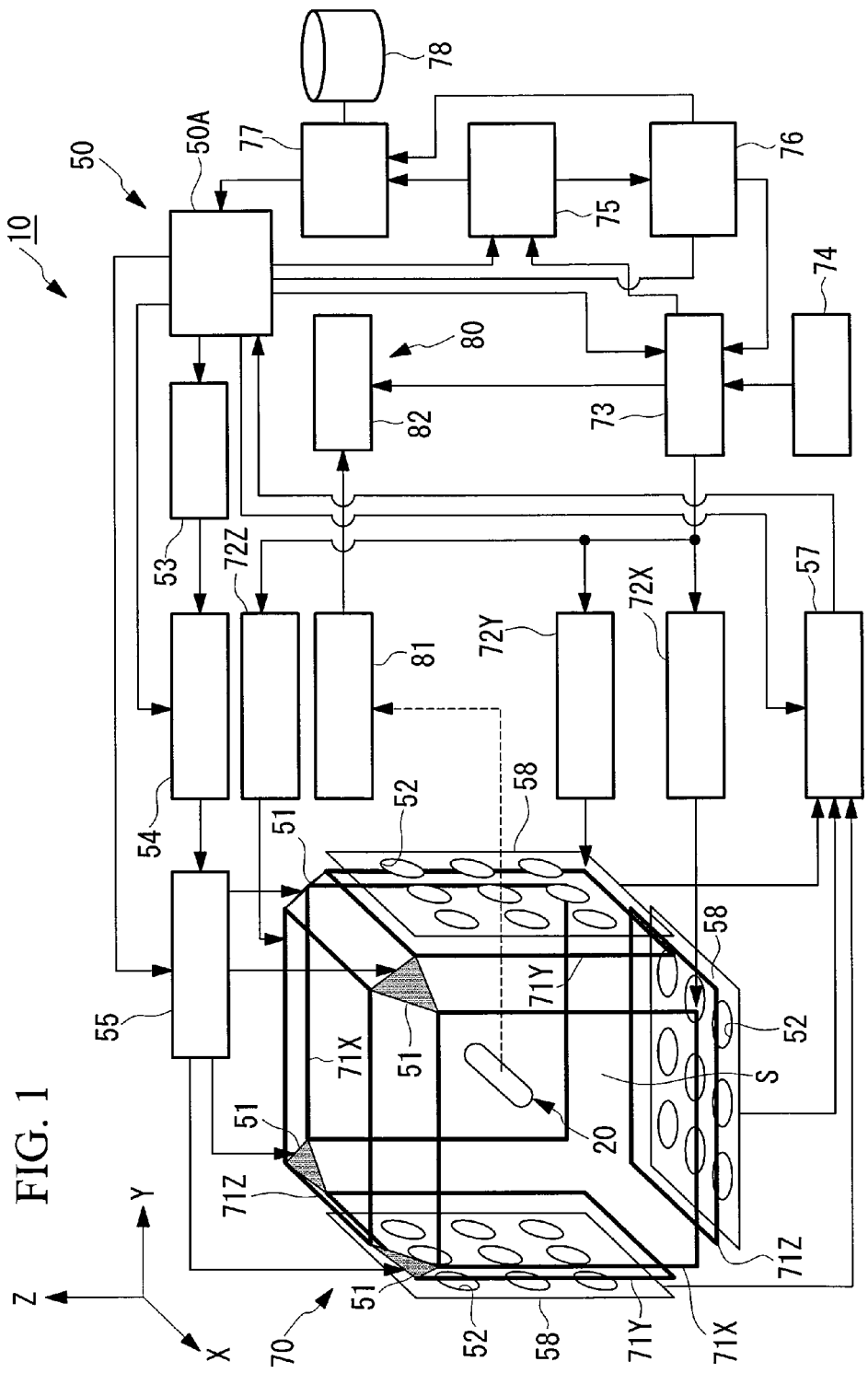
FIG. 1 is a schematic diagram showing a capsule endoscope guiding system according to a first embodiment of the present invention.

M: external magnetic field
S: operation region (operation range)
R: longitudinal axis
θ: magnetic field angle
10, 100, 120: capsule endoscope guiding system (medical device guiding system)
20, 20': capsule endoscope (medical device)
20": insertion portion (medical device)
25: spiral unit (spiral mechanism)
41, 41A: core member (magnetic core)
42A: magnetic induction coil
43: resonance circuit
43': self-excited oscillation circuit (resonance circuit)
45: permanent magnet (magnet)
50, 50': position detecting system
50A: position detecting device (position information calculator)
51: drive coil (alternate magnetic field generating device)
52: sense coil (alternate magnetic field detecting device)
70: magnetic induction device (magnetic field generating device)
73: magnetic field control circuit (magnetic field control device)
75: magnetic field determining unit (external magnetic field information calculator)
76: magnetic field angle determining unit (magnetic field angle calculator)
77: frequency setting unit
78: storage unit
110: medical device guiding system

BEST MODE FOR CARRYING OUT THE INVENTION

Capsule Endoscope Guiding System

First Embodiment

A position detecting system, a detecting method and a medical device guiding system of a medical device according to a first embodiment of the present invention will be described hereunder with reference to FIGS. 1 to 14. The medical device of this embodiment is a capsule endoscope 20.

Figure 2:
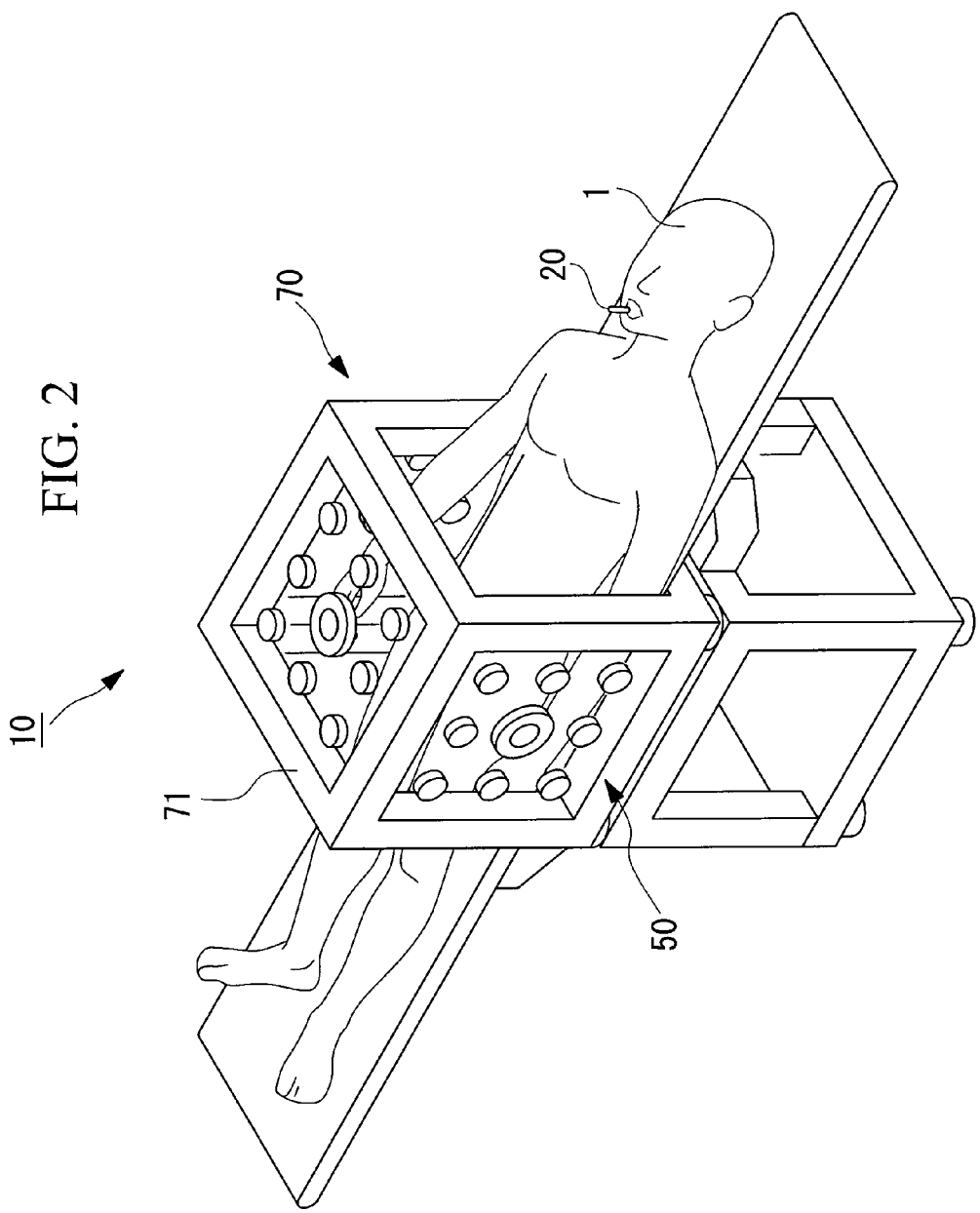
FIG. 2 is a perspective view showing the capsule endoscope guiding system of FIG. 1.

FIG. 1 is a diagram showing an outline of a capsule endoscope guiding system (medical device guiding system) 10 according to this embodiment. FIG. 2 is a perspective view showing the capsule endoscope guiding system 10.

As shown in FIGS. 1 and 2, the capsule endoscope guiding system 10 is equipped with a capsule endoscope (capsule medical device) 20 which is administered from a mouth portion or anus of a subject 1 into a body cavity, optically picks up an image of the inner wall surface of a coelomoduct and transmits an image signal wirelessly, a position detecting system 50 for detecting the position of the capsule endoscope 20, a magnetic induction device 70 for guiding the capsule endoscope 20 on the basis of the detected position of the capsule endoscope 20 and an instruction of a practitioner, and an image display device 80 for displaying the image signal transmitted from the capsule endoscope 20.

As shown in FIG. 1, the magnetic induction device 70 is equipped with a triaxial Helmholtz coil unit (magnetic generating device or external magnetic generating device) 71 for generating a parallel external magnetic field (rotational magnetic field) M for driving the capsule endoscope 20, a Helmholtz coil driver 72 for controlling amplification of current to be supplied to the triaxial Helmholtz coil unit 71, a magnetic field control circuit (magnetic field control device or external magnetic field generating device) 73 for controlling the direction of the external magnetic field M for driving the capsule endoscope 20, and an input device 74 for outputting the travel direction of the capsule endoscope 20 input by the practitioner to the magnetic field control circuit 73.

In this embodiment, the triaxial Helmholtz coil unit 71 is represented, however, it does not necessarily satisfy the condition of the Helmholtz coil strictly. For example, the coil is not circular, but it may be substantially rectangular as shown in FIG. 1, and the interval between the confronting coils may be out of the condition of the Helmholtz coil insofar as it satisfies the function of this embodiment.

As shown in FIGS. 1 and 2, the triaxial Helmholtz coil unit 71 is formed in a substantially rectangular shape. Furthermore, the triaxial Helmholtz coil unit 71 is equipped with three sets of Helmholtz coils (electromagnets) 71X, 71Y, 71Z which face one another, and each set of the Helmholtz coils 71X, 71Y, 71Z are disposed substantially vertically to the X, Y, Z axes of FIG. 1. The Helmholtz coils disposed substantially vertically to the X, Y, Z axes are represented by Helmholtz coils 71X, 71Y, 71Z respectively in this order.

The Helmholtz coils 71X, 71Y, 71Z are disposed so as to form a space S having a substantially rectangular parallelepiped therein. As shown in FIG. 1, the space S serves as an operation region (also called as operation region S) of the capsule endoscope 20, and also it servers as a space in which the subject 1 is placed as shown in FIG. 2.

The Helmholtz coil driver 72 has Helmholtz coil drivers 72X, 72Y, 72Z for controlling the Helmholtz coils 71X, 71Y, 71Z, respectively.

Data of a direction in which the capsule endoscope 20 is currently oriented (the direction of the longitudinal axis R of the capsule endoscope 20) is input from a position detecting device 50A (position information calculator) described later to the magnetic field control circuit 73, and a travel direction instruction of the capsule endoscope 20 input from the input device 74 by the practitioner is input to the magnetic field control circuit 73. Furthermore, signals for controlling the Helmholtz coil drivers 72X, 72Y, 72Z are output from the magnetic field control circuit 73, and also rotational phase data of the capsule endoscope 20 is output from the magnetic field control circuit 73 to the image display device 80. Furthermore, data of current to be supplied to each of the Helmholtz coil drivers 72X, 72Y, 72Z are output from the magnetic field control circuit 73.

Furthermore, in this embodiment, the magnetic field control circuit 73 receives a magnetic field angle θ from a magnetic field angle calculator 76 described later, and it is set to stop the control signals to the Helmholtz coil drivers 72X, 72Y, 72Z and extinguish an external magnetic field M when the magnetic field angle θ is smaller than a predetermined angle.

For example, a joy-stick (not shown) is provided as the input device 74, and the travel direction of the capsule endoscope 20 is indicated by tilting the joy-stick.

The joy-stick type as described above may be used as the input device 74, or another type input device such as an input device for indicating the travel direction by pushing the button of the travel direction may be used.

As shown in FIG. 1, the position detecting system 50 according to this embodiment comprises a drive coil 51 (external alternate magnetic field generating device) which generates an external alternate magnetic field for making a magnetic induction coil 42A (see FIG. 11) described later in the capsule endoscope 20 generate an induced magnetic field, a sense coil (alternate magnetic field detecting device) 52 for detecting the induced magnetic field (alternate magnetic field) generated by the magnetic induction coil 42A, and a position detecting device 50A for calculating the position information (position and direction) of the capsule endoscope 20 and controlling the alternate magnetic field formed by the drive coil 51 on the basis of the induced magnetic field detected by the sense coil 52.

The position detecting system 50 comprises a magnetic field determining unit 75 (external magnetic field information calculator) for calculating the intensity and direction of the external magnetic field M at the position of the capsule endoscope 20 on the basis of the current data output from the magnetic field control circuit 73 to the Helmholtz coil drivers 72X, 72Y, 72Z and the position data of the capsule endoscope 20 output from the position detecting device 50A, a magnetic field angle calculator 76 for calculating a magnetic field angle θ corresponding to an intersection angle between the direction of the external magnetic field M and the direction of the magnetic induction coil 42A (the direction of an alternate magnetic field generated by the magnetic induction coil 42A) on the basis of the direction of the external magnetic field M at the position of the capsule endoscope 20 calculated by the magnetic field determining unit 75 and the direction of the capsule endoscope 20 calculated by the position detecting device 50A, and a frequency setting unit 77 for estimating the resonance frequency of the resonance circuit 43 in the capsule endoscope 20 and determining the detection frequency on the basis of the magnetic field angle θ calculated by the magnetic field angle calculator 76 and the intensity of the external magnetic field M calculated by the magnetic field determining unit 75. The magnetic field angle θ is successively output from the magnetic field angle calculator 76 to the magnetic field control circuit 73.

In this embodiment, the position detecting system 50 is provided with the magnetic field determining unit 75. However, the intensity and direction of the external magnetic field M at the position of the capsule endoscope 20 may be directly received from the magnetic field control circuit 73 by the position detecting system 50. With this construction, the magnetic field determining unit may be omitted.

Furthermore, in this embodiment, the magnetic field angle calculator 76 for determining the magnetic field angle θ for calculating the intersection angle between the direction of the external magnetic field M and the direction of the induction coil 42A corresponding to the direction of the capsule endoscope 20 is provided, and the frequency of the external alternate magnetic field generated from the drive coil 51 is determined on the basis of the magnetic field angle and the intensity of the external magnetic field M. However, the operation may be carried out in the frequency setting unit 77 as described below. As a modification, the magnetic field intensity generated from the triaxial Helmholtz coil unit 71 may be controlled to be constant. By this control, the frequency of the external alternate magnetic field generated from the drive coil 51 can be determined on the basis of the magnetic field angle. Through the above control, the operation of the frequency setting unit 77 can be simplified. Furthermore, when the restraint of the capsule endoscope 20 by the living body is weak, the magnetic field angle is kept to a value near to 90° at all times. Under such a condition, the frequency of the external alternate magnetic field generated from the drive coil 51 can be determined on the basis of only the intensity of the external magnetic field M without using any information of the magnetic field angle. By this control, the operation of the frequency setting unit 77 can be simplified.

Equations which are described according to the Biot-Savart law to calculate the intensity and direction of the magnetic field created by the respective Helmholtz coils 71X, 71Y, 71Z at the point (X, Y, Z) in the space S are stored in the magnetic field determining unit 75, and when the value of current flowing into each of the Helmholtz coils 71x, 71Y, 71Z and the coordinate of the capsule endoscope 20 are input, the intensity and direction of the magnetic field generated by each of the Helmholtz coils 71X, 71Y, 71Z at the position of the capsule endoscope 20 are calculated. Then, by adding the magnetic fields generated by the respective Helmholtz coils 71X, 71Y, 71Z, the intensity and direction of the external magnetic field M generated at the position of the capsule endoscope 20 can be determined.

In this embodiment, each of the Helmholtz coils 71X, 71Y, 71Z forms confronting coil, and thus substantially parallel external magnetic field M having substantially uniform intensity can be formed in the space S in which the capsule endoscope 20 exists. Therefore, only the relational expression representing the relationship between the current flowing into each of the Helmholtz coils 71X, 71Y, 71Z and the magnetic field generated by each of the Helmholtz coils 71X, 71Y, 71Z is stored in the magnetic field determining unit 75, the current flow flowing in each of the Helmholtz coils 71X, 71Y, 71Z is obtained from the magnetic field control circuit 73, the intensity of the magnetic field generated by each of the Helmholtz coils 71X, 71Y, 71Z is calculated (the directions of the magnetic fields generated by the respective Helmholtz coils 71X, 71Y, 71Z are constant because of the parallel external magnetic field M), and the intensity and the direction of the external magnetic field M which is being currently generated is calculated from the above value. If the timing at which the current value flowing in each of the Helmholtz coils 71X, 71Y, 71Z is obtained from the magnetic field control circuit is set to the timing at which the position detecting device 50A carries out the position detection, the intensity and direction of the external magnetic field M can be more accurately determined.

Furthermore, in the magnetic control circuit 73, the relationship of the intensity and direction of the external magnetic field M acting on the capsule endoscope 20 with respect to the time is determined on the basis of past position information of the capsule endoscope 20, and the respective Helmholtz coil drivers 72X, 72Y, 72Z are controlled to generate the magnetic field in each of the Helmholtz coils 71X, 71Y, 71Z. Therefore, it holds the intensity and direction of the external magnetic field M generated at the position of the capsule endoscope 20 although it is based on the slight past data. This direction information may be directly transmitted from the magnetic field control circuit 73 to the magnetic field angle calculator 76, and the intensity information of the external magnetic field M may be directly transmitted from the magnetic field control circuit 73 to the frequency setting unit 77, whereby the magnetic field control circuit 73 is brought with the function of the magnetic field determining unit 75. With this construction, the error of the frequency determined in the frequency setting unit 77 may be slightly increased, however, it brings an effect of miniaturization of the device, simplification of the calculation, etc.

Here, the relationship between the state of the external magnetic field M and the variation of the frequency characteristic of the resonance circuit 43 in the capsule endoscope 20 will be described.

Figure 3:
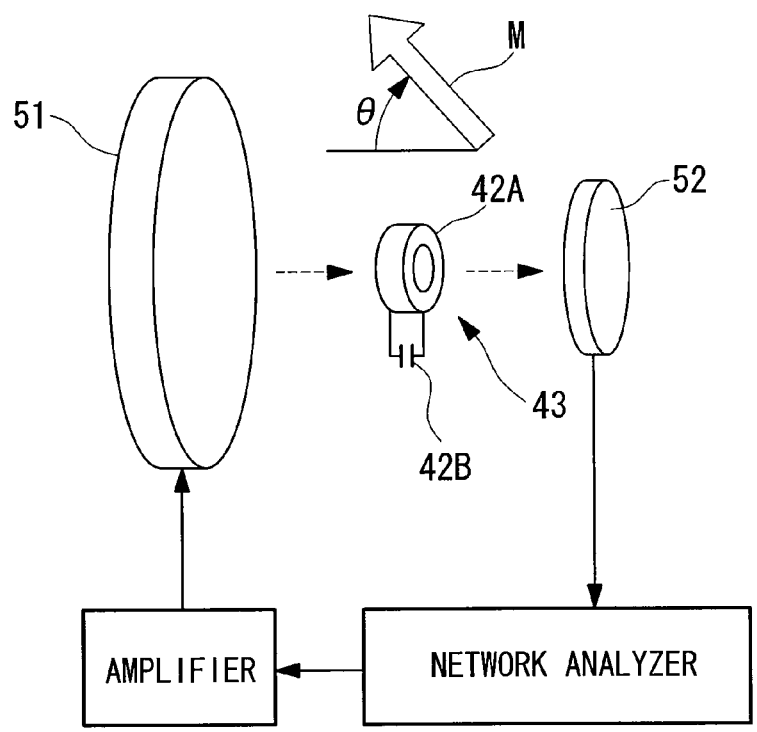
FIG. 3 is a diagram showing an example of a measuring method of measuring the frequency characteristic of a resonance circuit mounted in a capsule endoscope of the capsule endoscope guiding system of FIG. 1.
Figure 4:
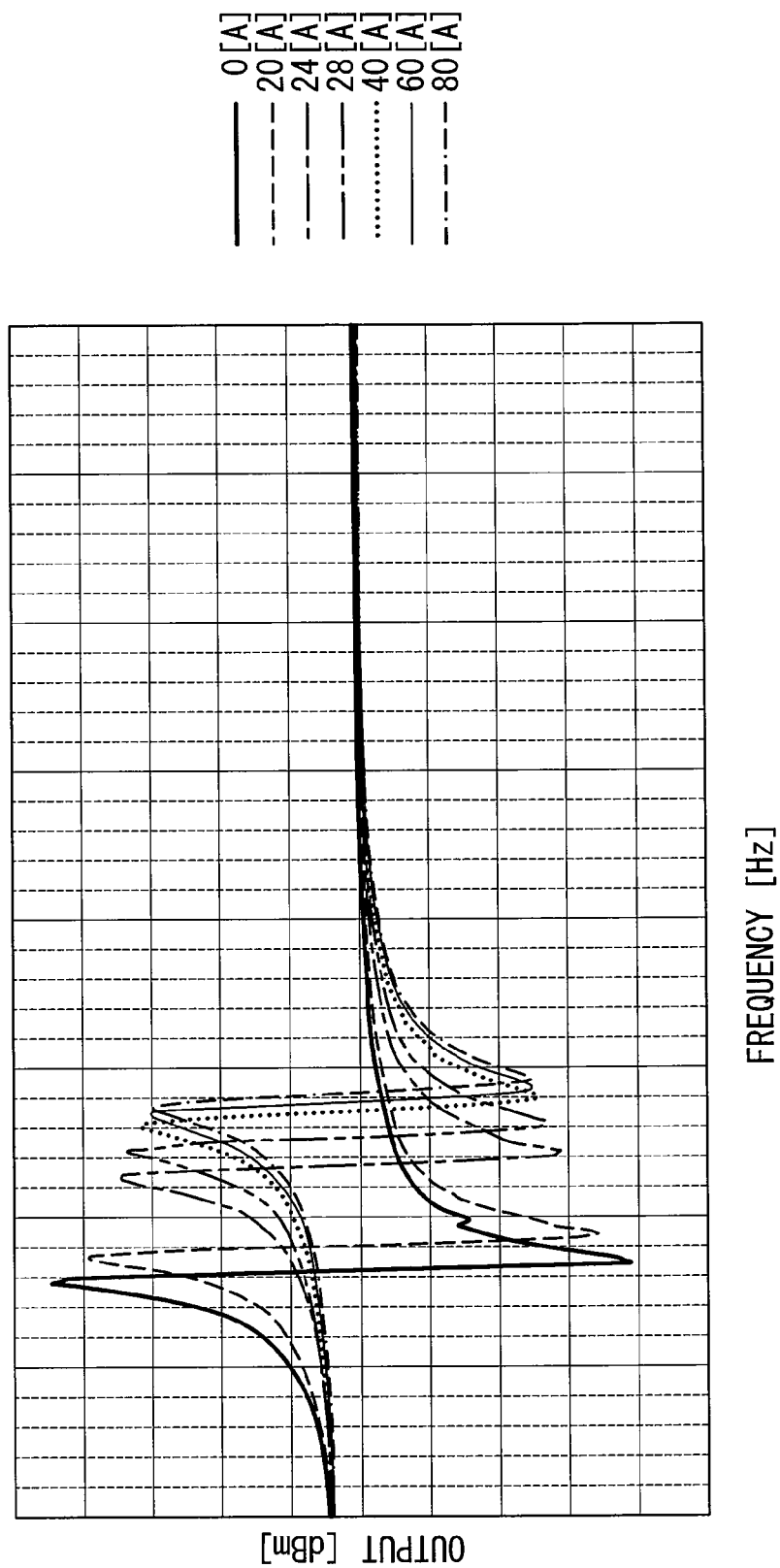
FIG. 4 is a graph showing a frequency characteristic containing the intensity of an external magnetic field measured by the measuring method of FIG. 3 as a parameter.

As shown in FIG. 3, the direction of the capsule endoscope 20 (the direction of the magnetic induction coil 42A of the resonance circuit 43) is aligned to the direction from the drive coil 51 to the sense coil 52, and further the intensity of the external magnetic field M is varied under the state that the direction of the external magnetic field M is set to the same direction (the magnetic field angle $\theta=0°$) the frequency is swept by a network analyzer and an amplifier, and the output of the sense coil 52 when the intensity of the external magnetic field M is varied is measured. FIG. 4 shows the result.

Figure 5:
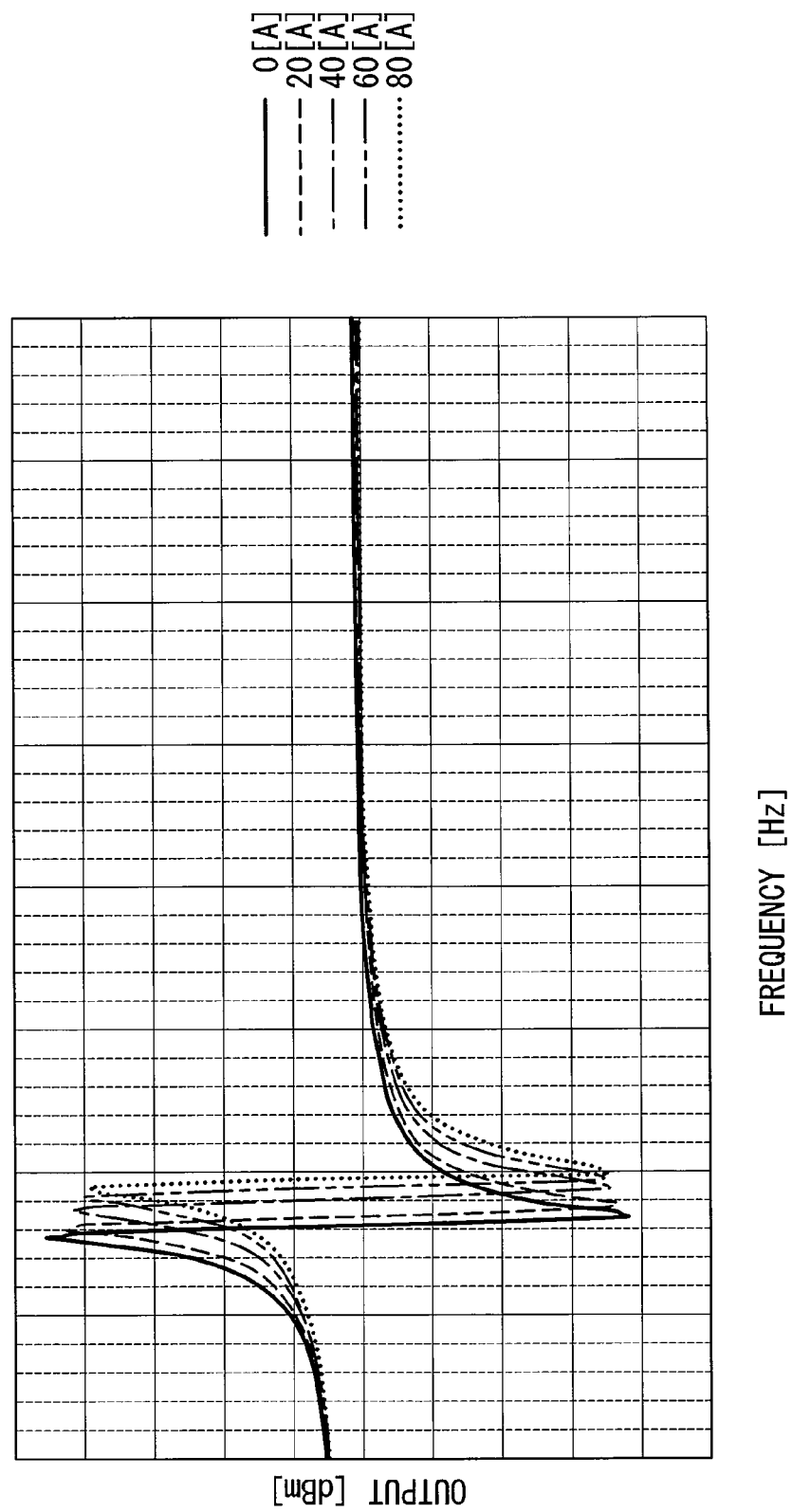
FIG. 5 is a graph showing another frequency characteristic containing the intensity of the external magnetic field measured by the measuring method of FIG. 3 as a parameter.

FIG. 5 shows a measurement result of the output of the sense coil 52 when the same measurement is likewise carried out under the state that the direction of the external magnetic field M is set to be perpendicular (the magnetic field angle $\theta=90°$).

Figure 6:
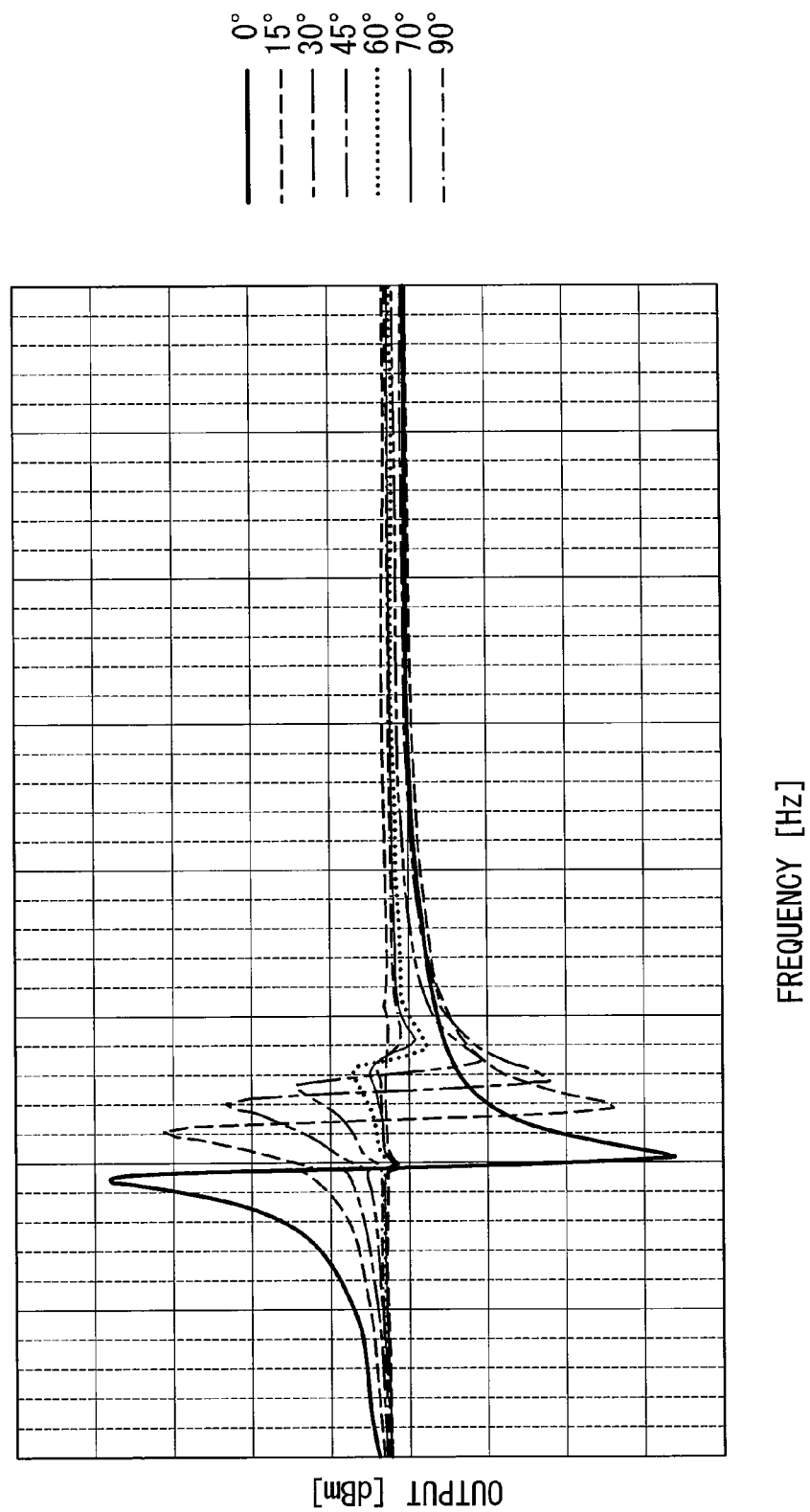
FIG. 6 is a graph showing the frequency characteristic containing a magnetic field angle measured by the measuring method of FIG. 3 as a parameter.

FIG. 6 shows a measurement result of the output of the sense coil 52 when the intensity of the external magnetic field M is fixed (to 80A) and the angle of the capsule endoscope 20 is varied to the magnetic field angle $\theta=0°$ under the same condition as the measurement of FIG. 5.

FIGS. 4 to 6 show the frequency characteristics of the resonance circuit 43 detected in the sense coil 52. In the resonance frequency of the resonance circuit 43, the output of the sense coil 52 is equal to zero, and the output is peaked at frequencies (peak frequencies) which are slightly displaced backward and forward from the output-zero point. It is apparent that the resonance frequency of the resonance circuit 43 at which the output of the sense coil 52 is equal to zero is shifted in accordance with the intensity of the external magnetic field M and the magnetic field angle $\theta$.

As is apparent from these results, even when the direction of the capsule endoscope 20 with respect to the external magnetic field M is kept to a fixed direction, the frequency characteristic of the resonance circuit varies when the intensity of the external magnetic field M varies, and thus the resonance frequency thereof is shifted. Furthermore, even when the intensity of the external magnetic field M is kept fixed, the frequency characteristic of the resonance circuit 43 varies when the magnetic field angle $\theta$ varies, and thus the resonance frequency thereof is shifted. The output is rapidly lowered in FIG. 6 because the magnetic induction coil 42A has an angle to the alternate magnetic field generated by the drive coil 51, the magnetic flux penetrating through the magnetic induction coil 42A is reduced, and the induced magnetic field generated by the magnetic induction coil 42A is reduced.

Figure 7:
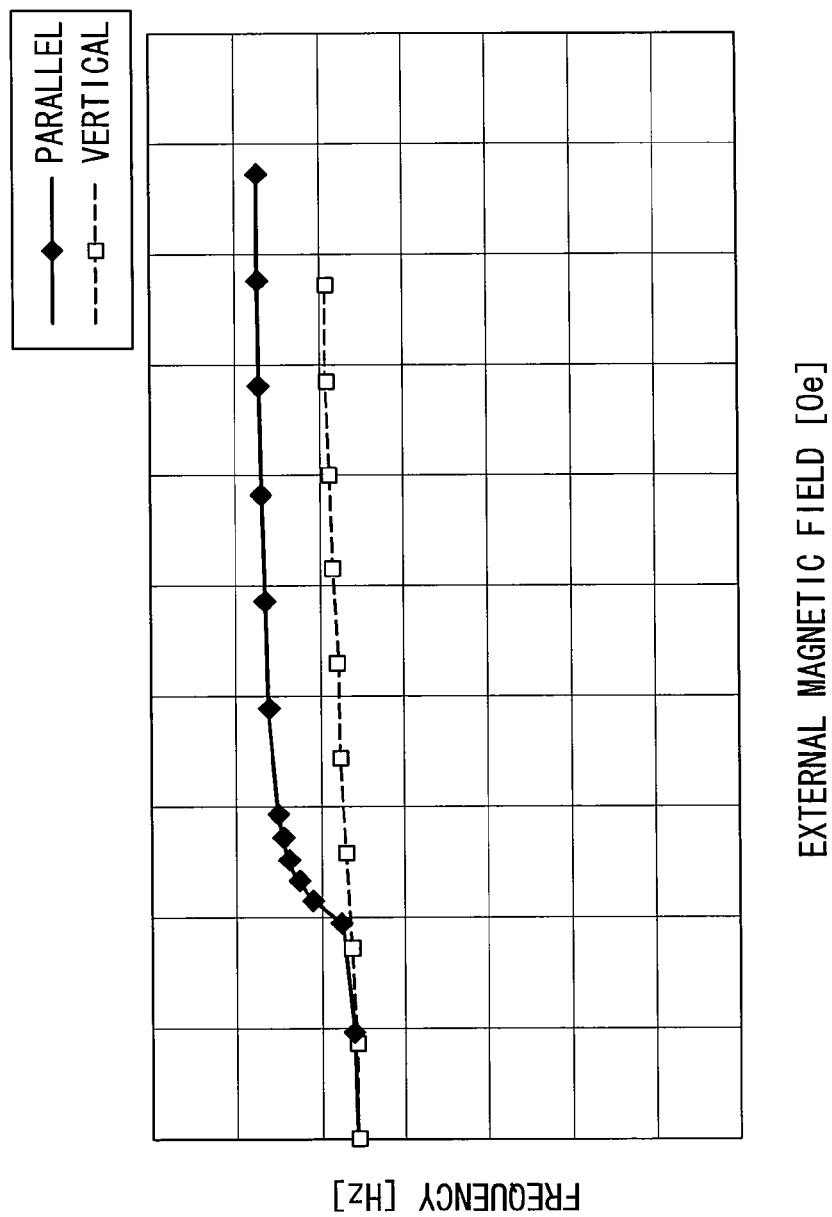
FIG. 7 is a graph in which peak frequencies of the frequency characteristics of FIGS. 4 and 5 are plotted and the plots are connected to one another by lines.
Figure 8:
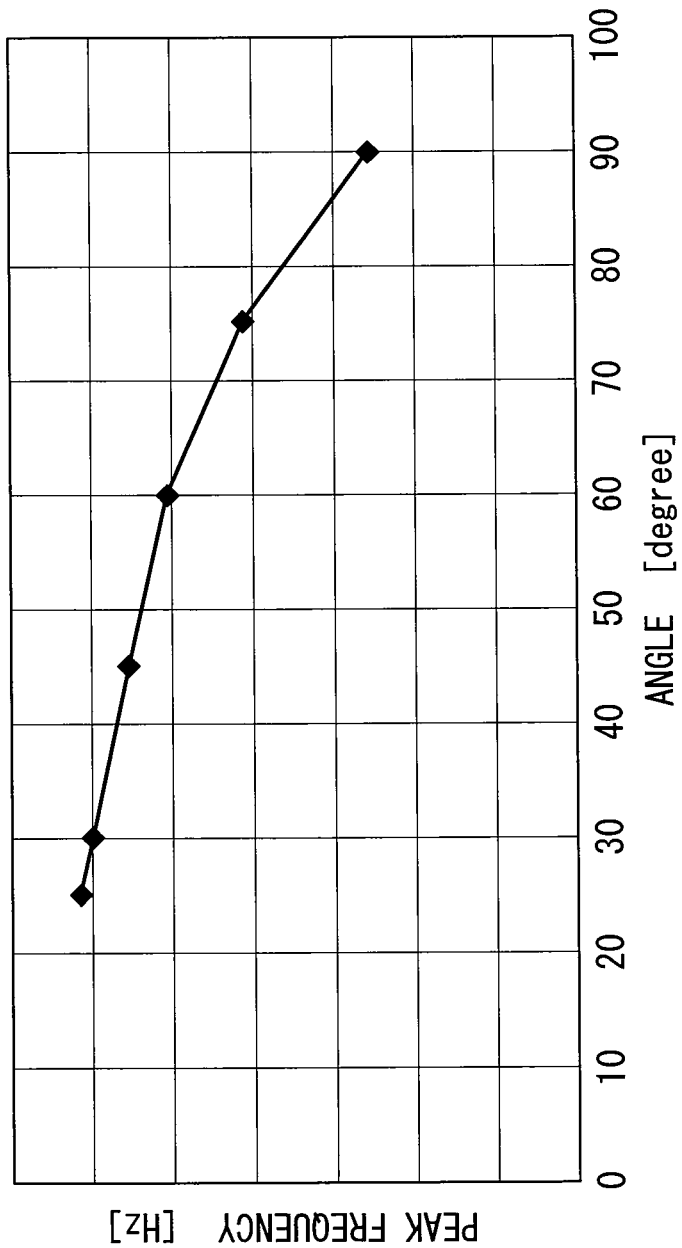
FIG. 8 is a graph in which peak frequencies of the frequency characteristic of FIG. 6 are plotted and the plots are connected to one another by a line.

FIG. 7 is a graph obtained by plotting the relationship between the peak frequencies of the frequency characteristics of FIGS. 4 to 6 and the intensity of the external magnetic field M. FIG. 8 is a graph obtained by plotting the relationship between the peak frequency of the frequency characteristic of FIG. 6 and the magnetic angle $\theta$.

Next, a method of setting the frequency in the frequency setting unit 77 will be described below. In this embodiment, the frequency setting unit 77 is equipped with a storage unit 78 for storing the resonance frequencies of the resonance circuit 43 shown in FIGS. 4 to 6 and the peak frequencies (detection frequencies) shown in FIGS. 7 and 8 in association with the intensity of the external magnetic field M and the magnetic field angle $\theta$. When the intensity of the external magnetic field M determined by the magnetic field determining unit 75 and the magnetic field angle $\theta$ determined by the magnetic field calculator 76 are input, the data stored in the storage unit 78 are referred to on the basis of the intensity of the external magnetic field M and the magnetic field angle $\theta$, and the corresponding resonance frequency and peak frequency are read out.

A method of storing data in a matrix form may be first used as a data storing method. That is, the intensity of the external magnetic field M and the magnetic field angle θ are set as two parameters, and the resonance frequency and peak frequency corresponding to each parameter are stored. Accordingly, when the intensity of the external magnetic field M and the magnetic field angle θ are input, the corresponding nearest resonance frequency and peak frequency are selected. This method is preferable in that the frequencies can be simply determined, however, the data amount is increased.

As a second method may be used a method of storing, as data, an approximate expression representing the relationship between the intensity of the external magnetic field M and the resonance frequency and the peak frequency every fixed magnetic field angle θ interval. For example, a relational expression representing the relationship between the intensity of the external magnetic field M and the frequency while the interval of the magnetic field angle θ is equal to 5° is created according to the expression 1.

$$f(H)|_{at=0°} = A_0 \times H^4 + B_0 \times H^3 + C_0 \times H^2 + D_0 \times H + E_0$$
$$f(H)|_{at=5°} = A_5 \times H^4 + B_5 \times H^3 + C_5 \times H^2 + D_5 \times H + E_5$$
$$\vdots$$
$$f(H)|_{at=90°} = A_{90} \times H^4 + B_{90} \times H^3 + C_{90} \times H^2 + D_{90} \times H + E_{90}$$

[Expression 1]

Here, $A_0$, $B_0$, $C_0$, $D_0$, $E_0$, $A_5$, $B_5$, $C_5$, $D_5$, $E_5$, ..., $A_{90}$, $B_{90}$, $C_{90}$, $D_{90}$, $E_{90}$ represent constants, and suffixes represent angles. H represents the intensity of the external magnetic field, and f represents the resonance frequency or peak frequency. This approximate expression is a polynomial approximate expression created by using the least-square method. The frequency setting unit 77 which stores this expression into the storage unit 78 determines that the approximate expression created at the angle nearest to the input magnetic field angle θ is used, and then substitutes the input intensity of the external magnetic field M into the selected expression to determine the resonance frequency and the peak frequency.

Furthermore, as a third method, the following approximate expression may be created as an approximate expression representing the relationship of the resonance frequency or the peak frequency, the intensity of the external magnetic field and the magnetic field angle θ.

$$f(\theta,H) = (A_\theta \times \theta^4 + B_\theta \times \theta^3 + C_\theta \times \theta^2 + D_\theta \times \theta + E_\theta) \times (A_H \times H^4 + B_H \times H^3 + C_H \times H^2 + D_H \times H + E_H)$$

[Expression 2]

Here, $A_\theta$, $B_\theta$, $C_\theta$, $D_\theta$, $E_\theta$, $A_H$, $B_H$, $C_H$, $D_H$, $E_H$ represent constants, suffix θ represents the magnetic field angle θ obtained form the magnetic field angle calculator, and suffix H represents the intensity of the external magnetic field M obtained from the magnetic field determining unit 75. By substituting the magnetic field angle θ and the intensity H of the external magnetic field M, the resonance frequency (or the peak frequency) f can be obtained. An example of the method of determining this expression is described below.

G is calculated according to the following expression by using the magnetic field angle $\theta_{mn}$, the intensity $H_{mn}$ of the external magnetic field M and the resonance frequency (or the peak frequency) $f_{mn}$ which were experimentally obtained. The suffix m represents the measurement, and the suffix n represents the frequency of the measurement (number).

$$G = \Sigma(f_{mn} - f(\theta_{mn}, H_{mn}))^2$$

[Expression 3]

This expression 3 is partially differentiated by $A_\theta$, $B_\theta$, $C_\theta$, $D_\theta$, $E_\theta$, $A_H$, $B_H$, $C_H$, $D_H$, $E_H$ to obtain differential equations, and simultaneous equations thereof are solved, whereby these constants $A_\theta$, $B_\theta$, $C_\theta$, $D_\theta$, $E_\theta$, $A_H$, $B_H$, $C_H$, $D_H$, $E_H$ can be determined. It may be possible to determine primary and secondary partial differentiations containing cross terms and carry out a repetitive convergent calculation such as the Newton method or the like to determine the respective constants $A_\theta$, $B_\theta$, $C_\theta$, $D_\theta$, $E_\theta$, $A_H$, $B_H$, $C_H$, $D_H$, $E_H$.

A signal generating circuit 53 for generating alternate current on the basis of the output from the position detecting device 50A, a drive coil driver 54 for amplifying the alternate current input from the signal generating circuit 53 on the basis of the output from the position detecting device 50A, and a drive coil selector 55 for supplying the alternate current to the drive coil 51 selected on the basis of the output from the position detecting device 50A are disposed between the position detecting device 50A and the drive coil 51 as shown in FIG. 1.

The signal generating circuit 53 generates a sine wave signal having a set frequency or a composite wave signal of plural sine wave signals of plural set frequencies.

A sense coil reception circuit 57 for extracting an amplification value from the alternate current containing position information of the capsule endoscope 20, etc. from the sense coil 52 on the basis of the output from the position detecting device 50A and outputting the extracted amplification value to the position detecting device 50A is disposed between the sense coil 52 and the position detecting device 50A.

The resonance frequency set by the frequency setting unit 77 is transmitted to the position detecting device 50A to make the frequency of the alternate magnetic field output from the signal generating circuit 53 coincident with the resonance frequency. The peak frequency determined by the frequency setting unit 77 is also transmitted to the sense coil reception circuit 57 to set the frequency of the alternate magnetic field received by the sense coil 52 to the peak frequency.

When only one type of magnetic induction coils 42A of the resonance circuit 43 are provided and the individual difference among them is small, it may be stored as preset data in the storage unit 78. When plural types of magnetic induction coils 42A are provided, however, the individual difference among them is small, plural kinds of data may be stored as preset data in the storage unit 78, and identification data representing the type of the magnetic induction coil 42A is read out manually or by a code reading device, thereby selecting proper preset data.

Furthermore, when the individual difference among the magnetic induction coils 42A is large, the data may be held as an identification code described in the package of the capsule endoscope so that the code of the package is read out by a reading device in use. Furthermore, in addition to the recording of the data as codes, the data may be described in RFID or a memory of the capsule endoscope.

Figure 9:
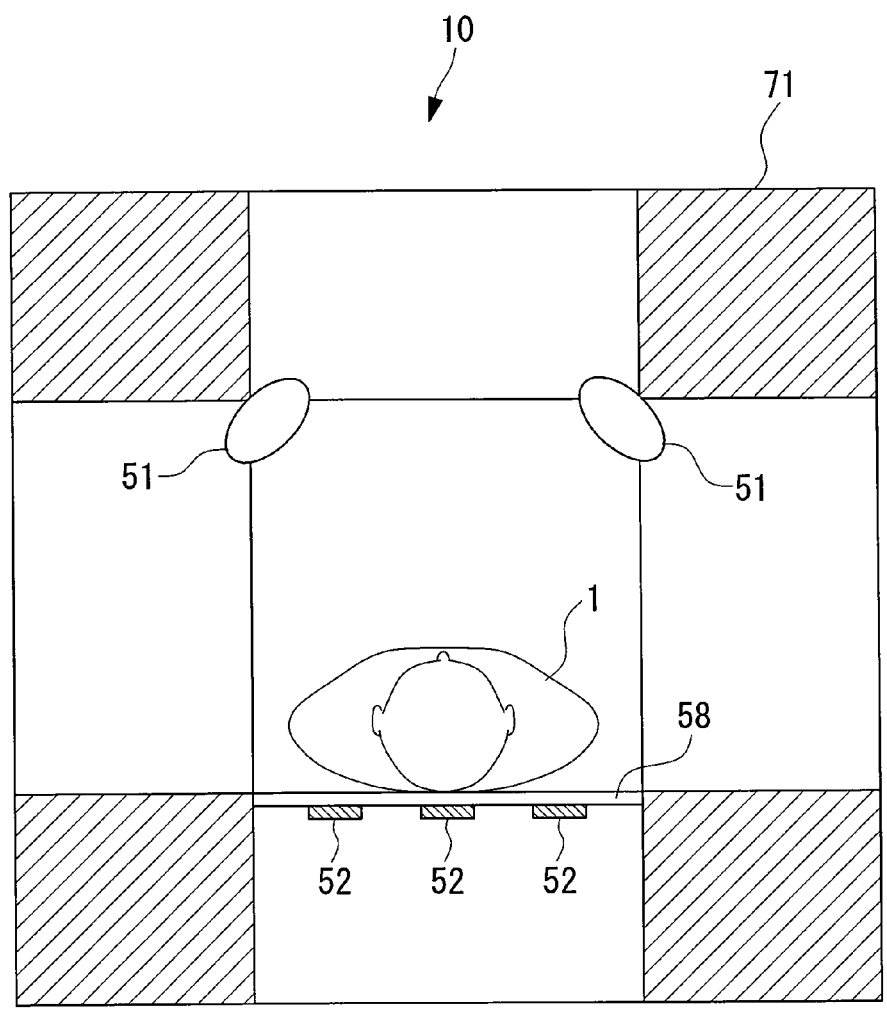
FIG. 9 is a schematic diagram showing the section of the capsule endoscope guiding system of FIG. 1.

FIG. 9 is a schematic diagram showing the cross-section of the capsule endoscope guiding system 10. Here, as shown in FIGS. 1 and 9, the drive coils 51 are obliquely disposed at four corners of the upper side (the forward side of the Z-axis) of the substantially rectangular parallelepiped operation region formed by the Helmholtz coils 71X, 71Y, 71Z. The drive coils 51 are formed as substantially triangular coils each of which connects the corner portions of the rectangular Helmholtz coils 71X, 71Y, 71Z. As described above, the drive coils 51 are disposed at the upper side, whereby the interference between the drive coils 51 and the subject 1 can be prevented.

The drive coils 51 may be designed as substantially triangular coils as described above, or they may be designed in a circular shape or other various shapes.

Furthermore, the sense coils 52 are formed as air core coils, and they are supported by three planar coil supporting members 58 which are disposed at the inside of the Helmholtz coils 71X, 71Y, 71Z so as to face the drive coils 51 through the operation region S of the capsule endoscope 20 and also face one another in the Y-axis direction. Nine sense coils 52 are arranged in a matrix form on one coil supporting member 58, and the position detecting system 50 is provided with twenty seven sense coils 52 as a whole.

The sense coils 52 may be located on the same planes as the Helmholtz coils 71X, 71Y, 71Z or at the outside of the Helmholtz coils 71X, 71Y, 71Z, and they may be freely disposed in any arrangement.

Figure 10:
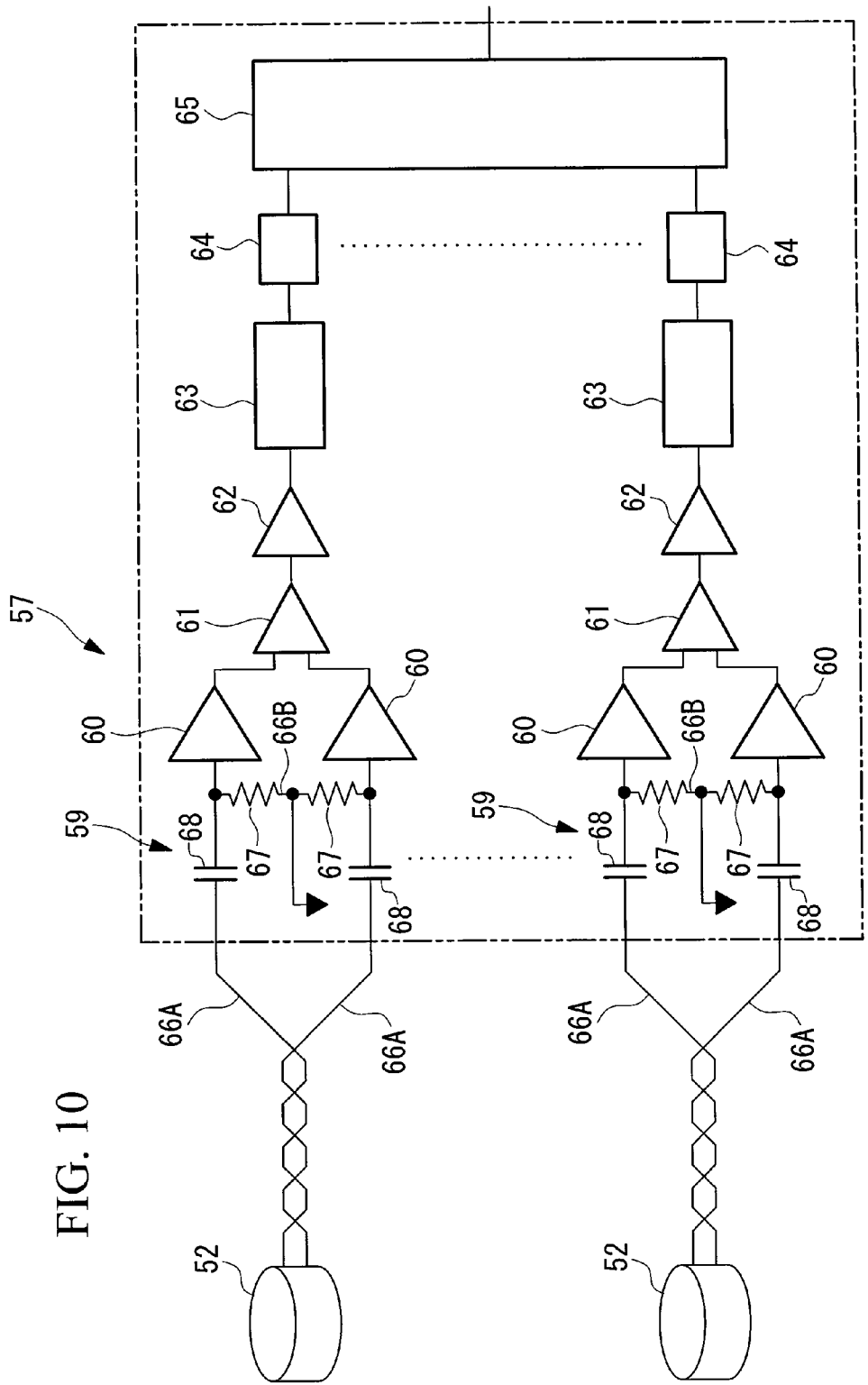
FIG. 10 is a schematic diagram showing a circuit construction of a sense coil reception circuit of the capsule endoscope guiding system of FIG. 1.

FIG. 10 is a schematic diagram showing the circuit construction of a sense coil reception circuit 57.

As shown in FIG. 10, the sense coil reception circuit 57 comprises high-pass filters (HPF) 59 for removing a low-frequency component of an alternate voltage based on an induced magnetic field containing the position information of the capsule endoscope 20 which is input to the sense coil 52, pre-amplifiers 60 for amplifying the alternate voltage, band-pass filters (BPF, band limiting unit) 61 for removing a high-frequency component contained in the amplified alternate voltage, amplifiers (AMP) 62 for amplifying the alternate voltage from which the high-frequency component is removed, effective value detecting circuits (True RMS comparators) 63 for detecting the amplitude of the alternate voltage to detect the amplitude value, and outputting the amplitude value, A/D converters 64 for converting the amplitude value to a digital signal, and a memory 65 for temporarily storing the digitalized amplitude value.

Here, the high-pass filter (HPF) 59 also serves to remove a low-frequency signal induced in the sense coil 52 by the rotational magnetic fields generated by the Helmholtz coils 71X, 71Y, 71Z, whereby the position detection system 50 is allowed to operate normally under the state that the magnetic induction device 70 is operated.

The high-pass filter 59 comprises resistors 67 disposed in a pair of wires 66A extending from the sense coil 52, a wire 66B which connects the pair of wires 66A and is grounded substantially at the center thereof, and a pair of capacitors 68 disposed so as to face the wire 66B through the ground point. The pre-amplifiers 60 are disposed in a pair of wires 66A respectively, and the alternate voltages output from the pre-amplifiers 60 are input to one band pass filter 61. The memory 65 temporarily stores the amplitude value obtained from the nine sense coils 52, and outputs the stored amplitude value to the position detecting device 50A.

In addition to these elements, a common mode filter which can remove noises of common mode may be provided.

As described above, the effective value detection circuits 63 may be used to extract the amplitude value of the alternate voltage, or the amplitude value may be detected by smoothing magnetic information through a rectifying circuit and detecting the voltage.

With respect to the waveform of the alternate voltage to be detected, the phase to the waveform added to the drive coil 51 is varied in accordance with the presence or absence, the position of the magnetic induction coil 42A. This phase variation may be detected by a lock-in amplifier or the like.

As shown in FIG. 1, the image display device 80 comprises an image reception circuit 81 for receiving image information transmitted from the capsule endoscope 20, and a display unit 82 for displaying an image on the basis of the received image information and the signal from the magnetic field control circuit 73.

As shown in FIG. 1, in the image display device 80, the image reception circuit 81 receives a compressed image signal from the capsule endoscope 20, and the image signal is output to the display unit 82. The compressed image signal is restored in the image reception circuit 81 or the display unit 82, and displayed by the display unit 82.

Furthermore, the display unit 82 executes the rotation processing on the image signal in the opposite direction to the rotational direction of the capsule endoscope 20 on the basis of the rotational phase data of the capsule endoscope 20 input from the magnetic field control circuit 73, and then displays the image signal.

Figure 11:
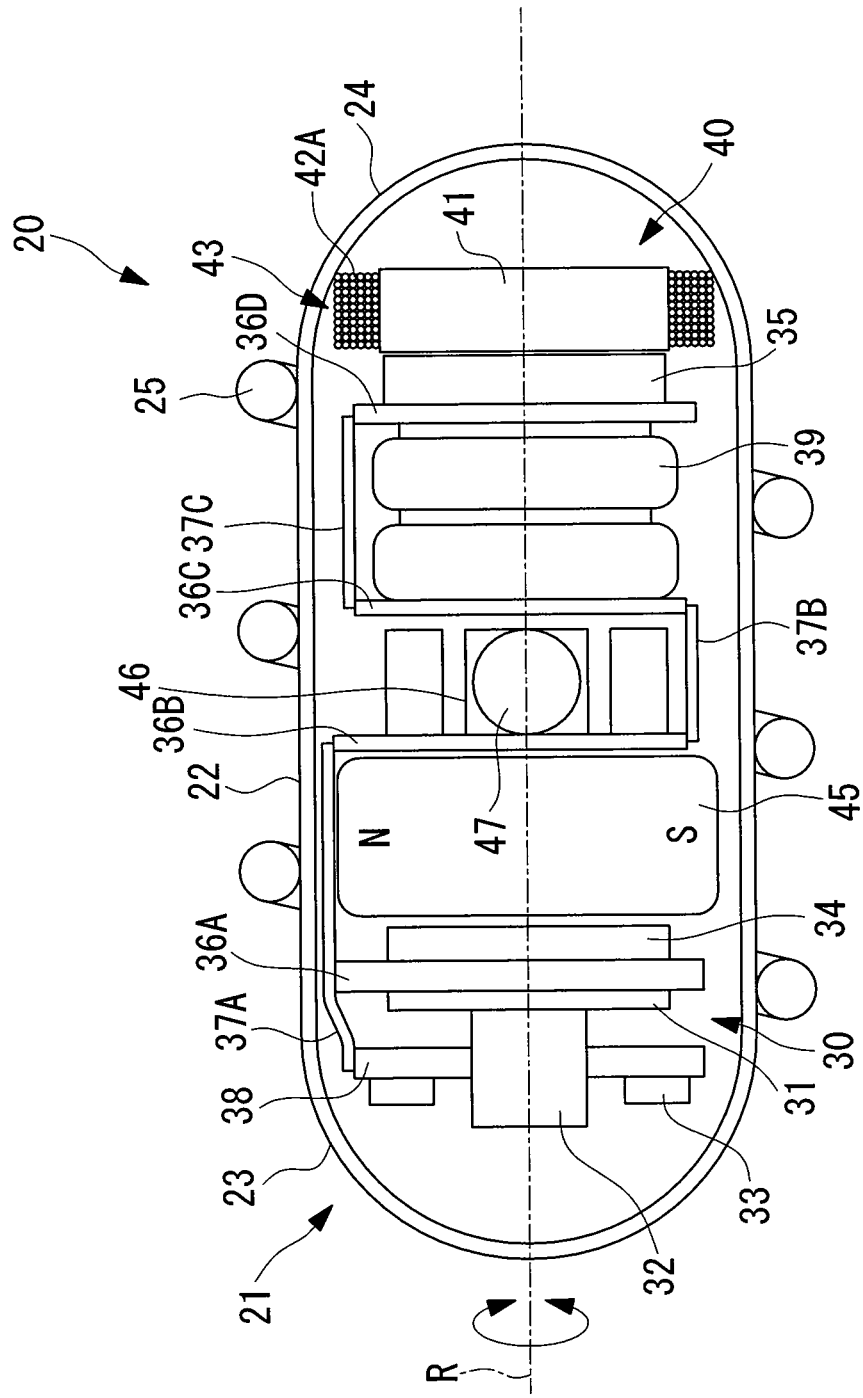
FIG. 11 is a schematic diagram showing the construction of the capsule endoscope of the capsule endoscope guiding system of FIG. 1.

FIG. 11 is a schematic diagram showing the construction of the capsule endoscope 20.

As shown in FIG. 11, the capsule endoscope 20 has an outer package 21 in which various kinds of equipment are accommodated, an image pickup unit 30 for picking up images of the inner wall surface of a coelomoduct of the subject 1, a battery 39 for driving the image pickup unit 30, an induced magnetic field generator 40 for generating an alternate magnetic field by the drive coils 51, and a permanent magnet (magnet) 45 for receiving the external magnetic field M generated by the magnetic induction device 70 and driving the capsule endoscope 20.

The outer package 21 is constructed by a cylindrical capsule main body (hereinafter referred to as main body) 22 which has a center axis as the longitudinal axis R of the capsule endoscope 20 and through which infrared light is transmitted, a semi-spherical transparent tip portion 23 covering the front end of the main body 22, and a semi-spherical rear end portion 24 covering the rear end of the main body, and the outer package 21 forms a hermetically-sealed capsule container having a water-tight structure.

A spiral unit (spiral mechanism) 25 is provided on the outer peripheral surface of the main body of the outer package 21 by winding a wire rod having a circular section in a spiral form around the outer peripheral surface with the longitudinal axis R as the center thereof.

When the permanent magnet 45 receives the rotating external magnetic field M generated by the magnetic induction device 70 and it is rotated, the spiral unit 25 is rotated around the longitudinal axis R together with the main body 22, so that the rotational motion of the main body 22 around the longitudinal axis R by the spiral unit 25 is converted to the linear motion in a direction along the longitudinal axis R. Therefore, the capsule endoscope 20 can be guided in the longitudinal axis R direction in the lumen.

The image pickup unit 30 comprises a board 36A disposed substantially vertically to the longitudinal axis R, an image sensor 31 disposed on a face at the tip portion 23 side of the board 36A, a lens group 32 for focusing an image of the inner wall surface of the coelomoduct of the subject 1 onto the image sensor 31, LED (Light Emitting Diode) 33 for illuminating the inner wall surface of the coelomoduct, a signal processor 34 disposed on the face at the rear end portion 24 side of the board 36A, and a wireless element 35 for transmitting an image signal to the image display device 80.

The signal processor 34 is electrically connected to the battery 39 through boards 36A, 36B, 36C, 36D and flexible boards 37A, 37B, 37C, electrically connected to the image sensor 31 through the board 36A, and electrically connected to LED 33 through the board 36A, the flexible board 37A and the supporting member 38. The signal processor 34 compresses an image signal obtained by the image sensor 31, temporarily stores the compressed image signal (into the memory), and transmits the compressed image signal from the wireless element 35 to the outside. In addition, the signal processor 34 controls ON/OFF of the image sensor 31 and LED 33 on the basis of a signal from a switching unit 46 described later.

The image sensor 31 converts an image focused through the tip portion 23 and the lens group 32 to an electrical signal (image signal), and outputs it to the signal processor 34. CMOS (Complementary Metal Oxide Semiconductor) or CCD may be used as the image sensor 31.

Plural LEDs 33 are arranged on the supporting member 38 disposed at the tip portion 23 side from the board 36A so as to be spaced from one another in the peripheral direction around the longitudinal axis R.

The permanent magnet 45 is disposed at the rear end portion 24 side of the signal processor 34. The permanent magnet 45 is disposed or magnetized so as to have a magnetization (magnetic poles) in a direction (for example, in the up-and-down direction of FIG. 5) perpendicular to the longitudinal axis R.

The switching unit 46 disposed on the board 36B is provided at the rear end portion 24 side of the permanent magnet 45. The switching unit 46 has an infrared sensor 47, and it is electrically connected to the signal processor 34 through the board 36B and the flexible board 37A and also electrically connected to the battery 39 through the boards 36B, 36C, 36D and the flexible boards 37B, 37C.

Plural switching units 46 are arranged at equal intervals in the peripheral direction around the longitudinal axis R, and also the infrared sensor 47 is disposed so as to face the outside in the radial direction. In this embodiment, an example in which four switching units 46 are arranged will be described. However, the number of switching units 46 is not limited to 4, and it may be any number.

The battery 39 is disposed at the rear end portion 24 side of the switching unit 46 so as to be sandwiched between the boards 36C and 36D.

The wireless element 35 is disposed on a surface at the rear end portion 24 side of the board 36D. The wireless element 35 is electrically connected to the signal processor 34 through the boards 36A, 36B, 36C, 36D and the flexible boards 37A, 37B, 37C.

The induced magnetic field generator 40 disposed at the rear end portion 24 side of the wireless element 35 is constructed by a core member (Magnetic core) 41 formed of ferrite formed in a cylindrical shape whose center axis is substantially coincident with the longitudinal axis R, a magnetic induction coil 42A disposed on the outer peripheral portion of the core member 41 and a capacitor 42B (not shown in FIG. 11) electrically connected to the magnetic induction coil 42A and forming the resonance circuit 43.

In addition to ferrite, a magnetic material is suitable for the core member 41, and iron, nickel, Permalloy, cobalt or the like may be used.

Figure 12A:
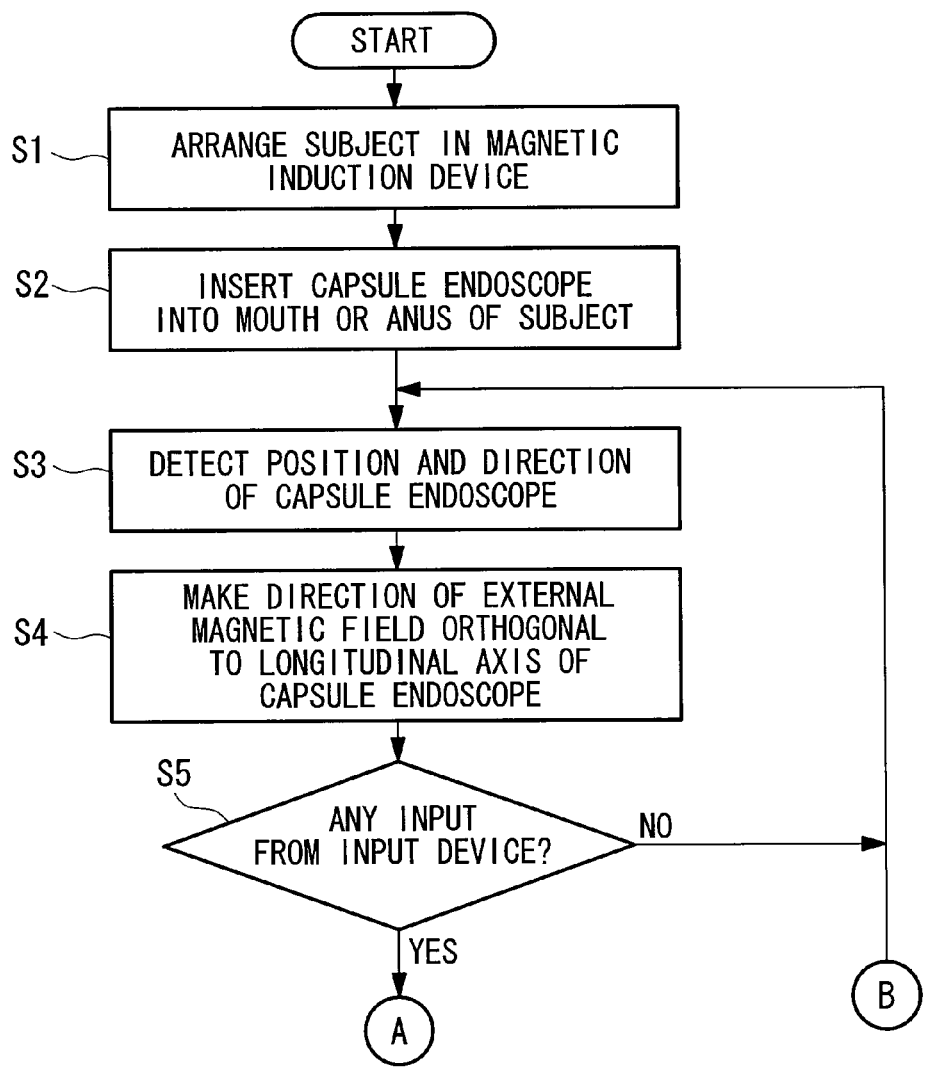
FIG. 12A is a flowchart showing a position detecting method of the capsule endoscope according to the embodiment of the present invention.

The action of the thus-constructed capsule endoscope guiding system 10 according to this embodiment will be described hereunder with reference with FIGS. 12A and 12B.

In order to guide the capsule endoscope 20 in a body cavity of a subject by using the capsule endoscope guiding system 10 of this embodiment to obtain an image of the body cavity, the subject 1 is first in a recumbent position in the space S inside the position detecting system 50 and the magnetic guide device 70 as shown in FIG. 2 (step S1). Subsequently, infrared light is applied to the infrared sensor 47 of the capsule endoscope 20 by an infrared light generating device (not shown), and the power of the capsule endoscope 20 is turned on (omitted in FIG. 12A). Then, the capsule endoscope 20 is administered into a body cavity of the subject 1 through the mouth portion or anus thereof (step S2).

Under this state, the position detecting system 50 is actuated, and the position and direction of the administered capsule endoscope 20 are detected (step S3). Subsequently, by the actuation of the magnetic field control circuit 73, the Helmholtz coil drivers 72X, 72Y, 72Z are controlled so that the external magnetic field M is generated in the direction perpendicular to the longitudinal axis R of the capsule endoscope 20 (step S4).

It is judged whether the practitioner operates the input device 74 or not (step S5). If the input device 74 is not operated, the steps S3 to S5 are repeated. On the other hand, when the input device 74 is operated, it is judge whether the operation concerned is an input for instructing the end or not (step S6). If it is not the end instruction, according to the input from the input device 74, the direction of the capsule endoscope 20 is changed or the Helmholtz coil drivers 72X, 72Y, 72Z are controlled by the magnetic field control circuit 73 so as to generate the external magnetic field M for rotating the capsule endoscope 20 around the longitudinal axis R (step S7).

The capsule endoscope 20 which is guided to the neighborhood of an affected site in the coelomoduct of the subject 1 by the magnetic induction device 70 picks up images of the inner wall surface of the coelomoduct during the guidance to the affected site and in the neighborhood of the affected site. The data of the inner wall surface of the coelomoduct and the data of the neighborhood of the affected site whose images are picked up are transmitted to the image display device 80. The image display device 80 displays the transmitted images on the display unit 82.

In this case, according to this embodiment, the position and direction of the capsule endoscope 20 are calculated by the position detecting device 50A (step S9), and by the magnetic field determining unit 75 provided to the position detecting system 50, the intensity and direction of the external magnetic field M are determined on the basis of the position data of the capsule endoscope 20 which are transmitted from the position detecting device 50A and the current data flowing in the respective Helmholtz coils 71X, 71Y, 71Z for generating the external magnetic field M which are transmitted from the magnetic field control circuit 73.

Furthermore, the magnetic field angle calculator 76 calculates the magnetic field angle θ corresponding to the intersection angle between the external magnetic field M and the alternate magnetic field induced by the magnetic induction coil 42A on the basis of the direction data of the capsule endoscope 20 transmitted from the position detecting device 50A and the direction data of the external magnetic field M transmitted from the magnetic field determining unit 75 (step S10).

In this case, it is judged whether the magnetic field angle θ is smaller than a predetermined angle (step S11). If it is smaller, that is, if the intersection angle between the external magnetic field M and the alternate magnetic field is greatly reduced from 90°, the generation of the external magnetic field M is stopped (step S12). Accordingly, the capsule endoscope 20 can be prevented in advance from being rotated under the state that the rotational axis of the external magnetic field M and the longitudinal axis R of the capsule endoscope 20 are greatly displaced from each other.

That is, by stopping the external magnetic field M, the resonance circuit 43 enables the position detection at the original resonance frequency or peak frequency (under the state that no external magnetic field M exists), and thus the accurate position detection can be performed. Therefore, the direction of the external magnetic field M generated when there is an input from the input device 74 again is set to be oriented to the direction perpendicular to the longitudinal axis R of the capsule endoscope (step S4), and after the input from the input device 74 is checked (steps S5, S6), the external magnetic field M is rotated (step S8). Accordingly, the external magnetic M is rotated under the state that the rotational axis of the external magnetic field M is substantially coincident with the longitudinal axis R of the capsule endoscope 20, so that the capsule endoscope 20 can be stably rotated with no waggle and properly propelled.

Then, when an input of changing the direction of the capsule endoscope 20 is made from the input device 74, the direction of the external magnetic field M is changed. When the restraint of the capsule endoscope 20 is weak, the direction of the capsule endoscope 20 is changed so that the direction of the permanent magnet 45 is coincident with the direction of the external magnetic field M. When the restraint of the capsule endoscope 20 by the body cavity or the like is strong, the direction of the external magnetic field M and the direction of the longitudinal axis R of the capsule endoscope 20 are displaced from the orthogonal state, and the magnetic field angle θ satisfies θ<90°. Therefore, a torque for changing the direction of the capsule endoscope 20 is generated according to this displacement. When the torque is larger than the restraint force, the capsule endoscope 20 changes its direction. When the restraint force is large and thus the capsule endoscope 20 cannot change the direction, the magnetic field angle θ is smaller than a predetermined angle, and thus the processing goes to step S11 again to reset the operation again.

When the magnetic field angle θ is larger than the predetermined angle and near to 90°, the resonance frequency and/or the peak frequency stored in the storage unit 78 are read out on the basis of the intensity of the external magnetic field M output from the magnetic field determining unit 75 and the magnetic field angle θ output from the magnetic field angle calculator 76, and transmitted to the position detecting device 50A and the sense coil reception circuit 57 (step S13).

The position detecting device 50A outputs the above transmitted resonance frequency to the signal generating circuit 53 as the frequency of an alternate signal to be generated. The signal generating circuit 53 outputs to the drive coil driver 54 the alternate signal whose frequency is coincident with the resonance frequency transmitted from the position detecting device 50A. Even when the alternate signal generated by the drive coil driver 54 is slightly displaced from the resonance frequency, some degree of effect can be obtained. For example, when the resonance frequency is equal to 20.04 kHz and the frequency which can be generated by the signal generating circuit 53 is varied every 100 Hz, such as 19.9 kHz, 20 kHz, 20.1 kHz, the frequency generated by the signal generating circuit 53 may be set to 20 kHz. In this case, substantially the same effect as the case where the frequency is accurately conformed with the resonance frequency can be obtained.

The alternate signal is amplified in the drive coil driver 54, and output as alternate current to the drive coil selector 55. The amplified alternate current is supplied to the drive coil 51 selected by the position detecting device 50A in the drive coil selector 55. Then, the alternate current supplied to the drive coil 51 forms an alternate magnetic field in the operation region S of the capsule endoscope 20.

The alternate magnetic field thus formed makes the sense coils 52 and the magnetic induction coil 42A in the capsule endoscope 20 generates induced electromotive force. In this case, both of the alternate magnetic field based on the drive coil 51 and the alternate magnetic field induced in the magnetic induction coil 42A act on the sense coils 52, and the corresponding alternate voltages occur in the sense coils 52.

The magnetic induction coil 42A forms the resonance circuit 43 together with the capacitor 42B. Therefore, when the frequency of the alternate magnetic field is coincident with the resonance frequency of the resonance circuit 43, the induced electromotive force generated in the resonance circuit 43 (magnetic induction coil 42A) is large, and the formed alternate magnetic field is strong. Furthermore, the core member 41 formed of ferrite having dielectric property is disposed at the center of the magnetic induction coil 42A, so that magnetic fields can be easily collected at the core member 41 and the induced alternate magnetic field is further strong.

The alternate voltage generated in the sense coil 52 is input to the sense coil reception circuit 57, and the amplitude value of the alternate voltage is extracted.

With respect to the alternate voltage input to the sense coil reception circuit 57, the low-frequency component contained in the alternate voltage is removed by the high pass filter 59, and amplified by the pre-amplifier 60. Thereafter, the high-frequency component is removed by the band pass filter 61, and amplified by the amplifier 62.

In this case, in this embodiment, the transmission frequency of the band pass filter 61 is adjusted so as to be equal to the peak frequency transmitted from the position detecting device 50A. The amplitude value of the alternate voltage from which unnecessary components are removed as described above is extracted by the effective value detecting circuit 63. The extracted amplitude value is converted to a digital signal by the A/D converter 64, stored in the memory 65 and then transmitted to the position detecting device 50A.

The position detecting device 50A calculates the position and direction of the capsule endoscope 20 on the basis of the output of each sense coil 52 which is transmitted from the sense coil reception circuit 57.

Specifically, the position detection device 50A calculates the position and direction of the capsule endoscope 20 by solving simultaneous equations associated with the position and direction of the capsule endoscope 20 and the intensity of magnetic field on the basis of the amplitude of the alternate magnetic field obtained from the selected sense coil 52.

It is judged whether the end instruction is made from the input device 74 by the practitioner (step S14). If it is not input, the steps S8 to S14 are repeated, and if the end instruction is input, the operation is interrupted, and the position detecting operation and the guiding operation are finished.

For example, as the information of the position and direction of the capsule endoscope 20 are used totally six information of the position coordinates of X, Y, Z, the direction of the longitudinal axis of the capsule endoscope 20 (two angles) and the intensity of the induced magnetic field formed by the magnetic induction coil 42A.

In order to estimate these six information pieces by calculation, outputs from at least six sense coils 52 are required.

The number of the sense coils 52 may be set to six or more in this embodiment. However, if it is set to about 10 to 15, the position calculation error can be suppressed to a small value. Furthermore, as a method of selecting the sense coil 52, the outputs of all the sense coils 52 which are caused by the alternate magnetic field generated by the magnetic field induction coil 42A may be determined by calculation, and a required number of sense coils 52 having large outputs may be selected.

Furthermore, the data of the calculated position and direction of the capsule endoscope 20 may be output to other devices or the display unit 82.

Figure 13:
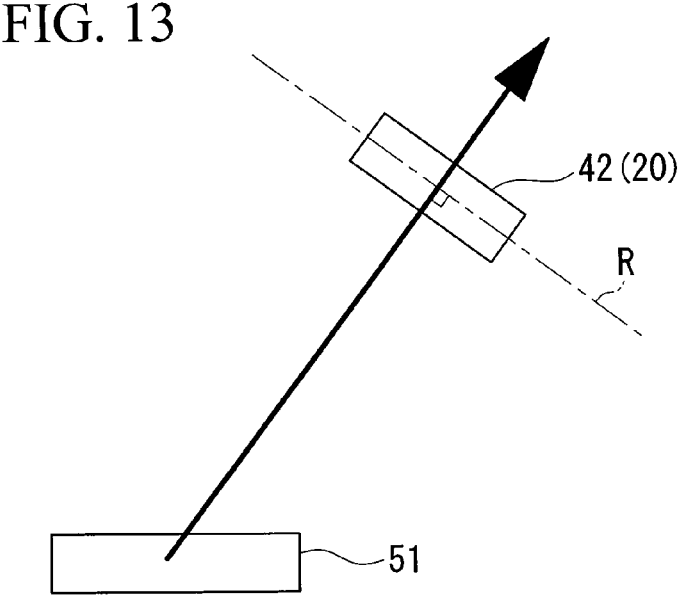
FIG. 13 is a diagram showing an arrangement relationship of a drive coil and a magnetic induction coil.
Figure 14:
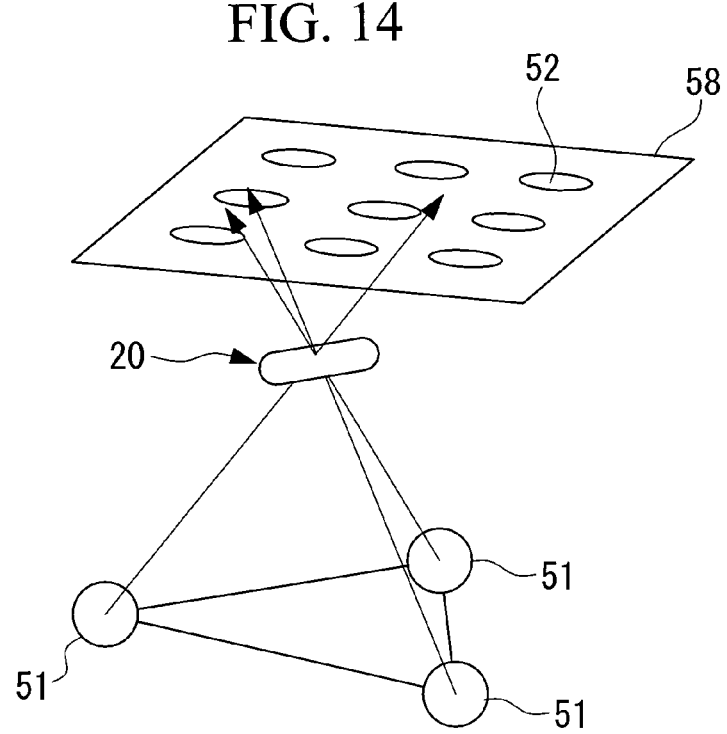
FIG. 14 is a diagram showing an arrangement relationship of the drive coil and a sense coil.

Furthermore, in parallel to the above control, the position detecting device 50A selects the drive coil 51 forming the alternate magnetic field and outputs an instruction to the drive coil selector 55 to supply alternate current to the selected drive coil 51. As shown in FIG. 13, the selection of the drive coil 51 is carried out by using a method of excluding a drive coil 51 with which a line connecting the drive coil 51 and the magnetic induction coil 42A (the direction of the drive coil 51) and the center axial line of the magnetic induction coil 42A (the longitudinal axis R of the capsule endoscope 20) are substantially orthogonal to each other is removed, disposing the direction of the magnetic field acting on the magnetic induction coil 42A primarily independently and supplying alternate current to any one of three drive coils 51 or plural drive coils as shown in FIG. 14.

A method of excluding a drive coil 51 with which the direction of the magnetic field lines formed by the drive coil 51 is substantially orthogonal to the center axial line of the magnetic induction coil 42A is more effective as a more preferable method.

As described above, the number of drive coils 51 forming the alternate magnetic field may be restricted by using the drive coil selector 55, or the arrangement number of the drive coils 51 may be set to three from the first drive coil 51 without using the drive coil selector 55.

Figure 15:
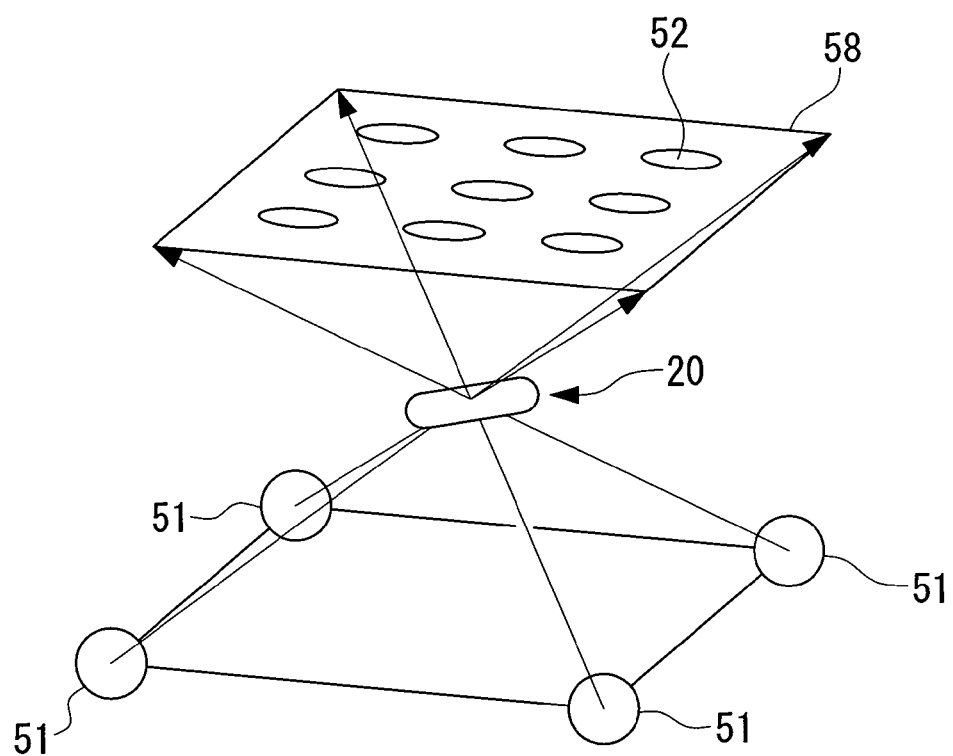
FIG. 15 is a diagram showing another arrangement relationship of the drive coil and the sense coil.

As described above, three drive coils 51 may be selected to form alternate magnetic field, or the alternate magnetic field may be generated by all the drive coils 51 as shown in FIG. 15.

Here, the switching operation of the drive coils 51 will be described more specifically.

The switching operation of the drive coils 51 is carried out as a countermeasure to occurrence of such a problem that the alternate magnetic field induced by the magnetic induction coil 42A would be reduced and thus the precision of the position detection would be reduced if the direction of the alternate magnetic field generated by the drive coil 51 and the direction of the magnetic induction coil 42A are vertical to each other at the position of the capsule endoscope 20.

The direction of the magnetic induction coil 42A, that is, the direction of the capsule endoscope 20 can be known from the output of the position detecting device 50A. Furthermore, the direction of the alternate magnetic field generated at the position of the capsule endoscope 20 by the drive coil 51 can be determined by the calculation. Accordingly, the intersection angle between the direction of the capsule endoscope 20 and the direction of the alternate magnetic field generated at the position of the capsule endoscope 20 by the drive coil 51 can be determined by the calculation.

Likewise, the directions of the alternate magnetic fields at the position of the capsule endoscope 20 which are generated by the drive coils 51 disposed at different positions and in different directions can be respectively determined by the calculation. Likewise, the intersection angle between the direction of the capsule endoscope 20 and the direction of the alternate magnetic field generated at the position of the capsule endoscope 20 by the respective drive coils 51 can be determined by the calculation.

Accordingly, by selecting the drive coil 51 with which the intersection angle between the direction of the capsule endoscope 20 and the direction of the alternate magnetic field generated at the position of the capsule endoscope 20 by the drive coil 51 is in acute-angle relationship with each other, the alternate magnetic field generated from the magnetic induction coil 42A can be kept large, and an excellent state can be kept to carry out position detection.

In order to select the drive coil 51, the direction of the alternate magnetic field generated at the position of the capsule endoscope 20 by the drive coil 51 is determined by the calculation. Subsequently, the intersection angle between the direction of the capsule endoscope 20 and the direction of the alternate magnetic field generated at the position of the capsule endoscope 20 by the drive coil 51 is calculated.

Likewise, the directions at the position of the capsule endoscope 20 of the alternate magnetic fields generated by the drive coils 51 disposed at different positions and in different directions are respectively calculated. Likewise, the intersection angle between the direction of the capsule endoscope 20 and the direction of the alternate magnetic field generated at the position of the capsule endoscope 20 by each drive coil 51 is calculated.

The drive coil 51 with which the intersection angle between the direction of the capsule endoscope 20 and the direction of the alternate magnetic field generated at the position of the capsule endoscope 20 by the drive coil 51 have the most acute-angle relationship is selected on the basis of the above calculation results. By selecting the drive coil 51 as described above, the alternate magnetic field generated from the magnetic induction coil 42A can be kept large, and the excellent state can be kept to perform the position detection.

By selecting the drive coil 51 as described above, the alternate magnetic field generated by the magnetic induction coil 42A can be efficiently detected by the sense coils 52 at all times under the condition that an alternate magnetic field which is as large as possible occurs. Therefore, the data amount used for the position calculation of the capsule endoscope 20 (magnetic induction coil 42A) can be reduced without losing the precision. Accordingly, the calculation amount can be reduced, and the system can be constructed at low cost. There is obtained such an effect that the system speed can be increased, etc.

Furthermore, with respect to the selection of the drive coil 51, two or more drive coils 51 may be selected. In this case, the alternate magnetic fields generated at the position of the capsule endoscope 20 (the magnetic induction coil 42A) by all the selected drive coils 51 are calculated, and the outputs of the respective drive coils 51 are adjusted so that the direction of the composite alternate magnetic field and the direction of the capsule endoscope 20 (magnetic induction coil 42A) are in acute-angle relationship with each other.

Still furthermore, the outputs of the drive coils 51 may be adjusted so that the intensities of the alternate magnetic fields at the position of the capsule endoscope 20 (magnetic induction coil 42A) generated by the drive coils 51 are constant or converged within some region.

By this adjustment, the alternate magnetic field generated from the magnetic induction coil 42A can be more stably output. Accordingly, the position detection can be implemented more accurately and more efficiently.

Still furthermore, as shown in FIG. 1, in the magnetic induction device 70, the practitioner inputs the guide direction of the capsule endoscope 20 to the magnetic field control circuit 73 through the input device 74. In the magnetic field control circuit 73, the direction and rotational direction of the external magnetic field M applied to the capsule endoscope 20 is determined on the basis of the input guide direction and the direction of the capsule endoscope 20 (longitudinal axis direction) input from the position detecting device 50A.

The intensity of the magnetic field generated by each of the Helmholtz coils 71X, 71Y, 71Z necessary to form the direction of the parallel magnetic field is calculated, and the current value required to generate this magnetic field is calculated.

The data of the current values supplied to the respective Helmholtz coils 71X, 71Y, 71Z are output to the corresponding Helmholtz coil drivers 72X, 72Y, 72Z, and the respective Helmholtz coil drivers 72X, 72Y, 72Z amplify current on the basis of input data, and supply the current to the corresponding Helmholtz coils 71X, 71Y, 71Z.

The Helmholtz coils 71X, 71Y, 71Z supplied with current generate the magnetic fields corresponding to the respective current values, and these magnetic fields are combined with each other, thereby forming the external magnetic field M having the parallel magnetic field direction determined by the magnetic field control circuit 73.

The permanent magnet 45 is mounted in the capsule endoscope 20, and the attitude of the capsule endoscope 20 (the direction of the longitudinal axis R) is controlled by the force or the torque which are generated when the external magnetic field M acts on the permanent magnet 45. Furthermore, the rotational period of the external magnetic field M is controlled to range from 0 Hz to about several Hz, and also the rotational direction of the external magnetic field M is controlled, whereby the rotational direction around the longitudinal axis R of the capsule endoscope 20 is controlled and the travel direction and the travel speed of the capsule endoscope 20 are controlled.

As shown in FIG. 11, in the capsule endoscope 20, the infrared sensor 47 of the switching unit 46 is first irradiated with infrared light, and the switching unit 46 outputs a signal to the signal processor 34. When taking the signal from the switching unit 46, the signal processor 34 supplies current from the battery 39 to the image sensor 31, LED 33, the wireless element 35 and the signal processor 34 itself mounted in the capsule endoscope 20, and sets these elements to ON-state.

The image sensor 31 picks up an image of the wall surface of the coelomoduct of the subject 1 illuminated by LED 33, converts the image to an electrical signal and outputs the electrical signal to the signal processor 34. The signal processor 34 compresses the input image signal, temporarily stores the compressed image signal and outputs it to the wireless element 35. The compressed image signal input to the wireless element 35 is transmitted as electrical waves to the image display device 80.

Furthermore, the capsule endoscope 20 is rotated around the longitudinal axis R by the spiral unit 25 disposed on the outer periphery of the outer package 21, whereby the capsule endoscope 20 can move to the tip portion 23 side or the rear end portion 24 side. The moving direction is determined by the rotational direction around the longitudinal axis R and the rotational direction of the spiral unit 25. Accordingly, the rotational direction around the longitudinal axis R of the capsule endoscope 20 is controlled, whereby the direction of the propelling force acting on the capsule endoscope 20 can be controlled.

According to the capsule endoscope guiding system 10 of this embodiment, the strength and direction of the rotational magnetic field corresponding to the external magnetic field M acting on the capsule endoscope 20 are varied, and even when the frequency characteristic of the resonance circuit 43 in the capsule endoscope 20 is varied in connection with the variation of the intensity and direction of the external magnetic field M, the resonance frequency and the peak frequency which are pre-stored in the storage unit 78 on the basis of the intensity of the external magnetic field M and the magnetic field angle θ are successively called, and the called peak frequency is set as the frequency to be detected by the sense coil 52, so that the reduction of the detection sensitivity can be prevented. Furthermore, the frequency of the alternate magnetic field generated by the drive coil 51 is also set to the called resonance frequency as described above, and thus the resonance circuit 43 in the capsule endoscope 20 can be kept to the resonance state irrespective of the state of the intensity of the external magnetic field M, etc., so that a larger alternate magnetic field can be generated and the detection sensitivity can be enhanced.

As a result, it is unnecessary to mount an element for adjusting the resonance frequency of the capsule magnetic induction coil 42A, etc., and thus the capsule medical device 20 can be miniaturized. Or, it is unnecessary to select or adjust the element such as the capacitor 42B constituting the resonance circuit 43 together with the magnetic induction coil 42A for the purpose of the adjustment of the resonance frequency, and the production cost of the capsule medical device 20 can be prevented from increasing.

Furthermore, the band pass filter 61 can limit the band of the output frequency of the sense coil 52 on the basis of the peak frequency transmitted from the position detecting device 50A. Therefore, the position and direction of the capsule medical device 20 can be calculated on the basis of the outputs of the sense coils 52 of the resonance frequency band, so that the time required for the calculation can be shortened.

The alternate magnetic fields are made to act on the magnetic induction coil 42A of the capsule endoscope 20 from three or more directions which are primarily independent of and different from one another. Therefore, the alternate magnetic field can be induced in the magnetic induction coil 42A by the alternate magnetic field from at least one direction irrespective of the direction of the magnetic induction coil 42A.

As a result, there is an effect that the magnetic induction coil 42A can be made to generate the alternate magnetic field at all times irrespective of the direction (longitudinal axis R direction) of the capsule endoscope 20, the alternate magnetic field can be detected by the sense coil 52 at all times and the position thereof can be accurately detected.

Furthermore, the sense coils 52 are disposed in different three directions with respect to the capsule endoscope 20. Therefore, irrespective of the arrangement position of the capsule endoscope 20, the external magnetic field having a detectable intensity acts on the sense coil 52 disposed at least one direction of the sense coils arranged in the three directions, and thus the alternate magnetic field can be detected by the sense coil 52 at all times.

Furthermore, the number of the sense coils 52 disposed in the above one direction is equal to nine, and thus sufficient inputs can be obtained so as to calculate totally six information of the X, Y, Z coordinates of the capsule endoscope 20, the rotational phases around the two axes which are orthogonal to the longitudinal axis R of the capsule endoscope 20 and also perpendicular to each other, and the intensity of the induced magnetization.

The drive coils 51 and the sense coils 52 are arranged so as to face one another through the operation region of the capsule endoscope 20. Therefore, the drive coils 51 and the sense coils 52 can be arranged without structurally interfering with each other.

By controlling the direction of the external magnetic field M acting on the permanent magnet 45 mounted in the capsule endoscope 20, the direction of the force acting on the permanent magnet 45 can be controlled, and the moving direction of the capsule endoscope 20 can be controlled. At the same time, the position of the capsule endoscope 20 can be detected, and the capsule endoscope 20 can be guided to a predetermined position. Accordingly, on the basis of the position of the detected capsule endoscope 20, the capsule endoscope 20 can be accurately guided.

By controlling the intensity of the external magnetic field generated from each of the three sets of Helmholtz coils 71X, 71Y, 71Z which are arranged so as to face one another in the orthogonal direction to one another, the direction of the external magnetic field occurring inside the Helmholtz coils 71X, 71Y, 71Z can be controlled to a predetermined direction. Therefore, the parallel external magnetic field M in a predetermined direction can be made to act on the capsule endoscope 20, and the capsule endoscope 20 can be moved in a predetermined direction.

Furthermore, the space S inside the Helmholtz coils 71X, 71Y, 71Z is a space in which the subject 1 can be disposed, and the drive coils 51 and the sense coils 52 are arranged around the space S. Therefore, the capsule endoscope 20 can be guided to a predetermined position in the body of the subject 1.

Furthermore, the image display device 80 executes the processing of rotating the image to be displayed in the rotational direction and opposite direction of the capsule endoscope 20 on the basis of the rotational phase information around the longitudinal axis R of the capsule endoscope 20. Therefore, irrespective of the rotational phase of the capsule endoscope 20, the image can be displayed on the display unit 82 as an image which stands still with a predetermined rotational phase at all times, that is, as if the capsule endoscope 20 travels in a direction along the longitudinal axis R without rotating around the longitudinal axis R.

Therefore, when the practitioner guides the capsule endoscope 20 while viewing the image displayed on the display unit 82, the practitioner can more easily view the image and more easily guide the capsule endoscope 20 to a desired position when a display image is displayed as an image of a predetermined rotational phase as described above as compared with a case where a display image is displayed as an image which rotates in connection with the rotation of the capsule endoscope 20.

Figure 16:
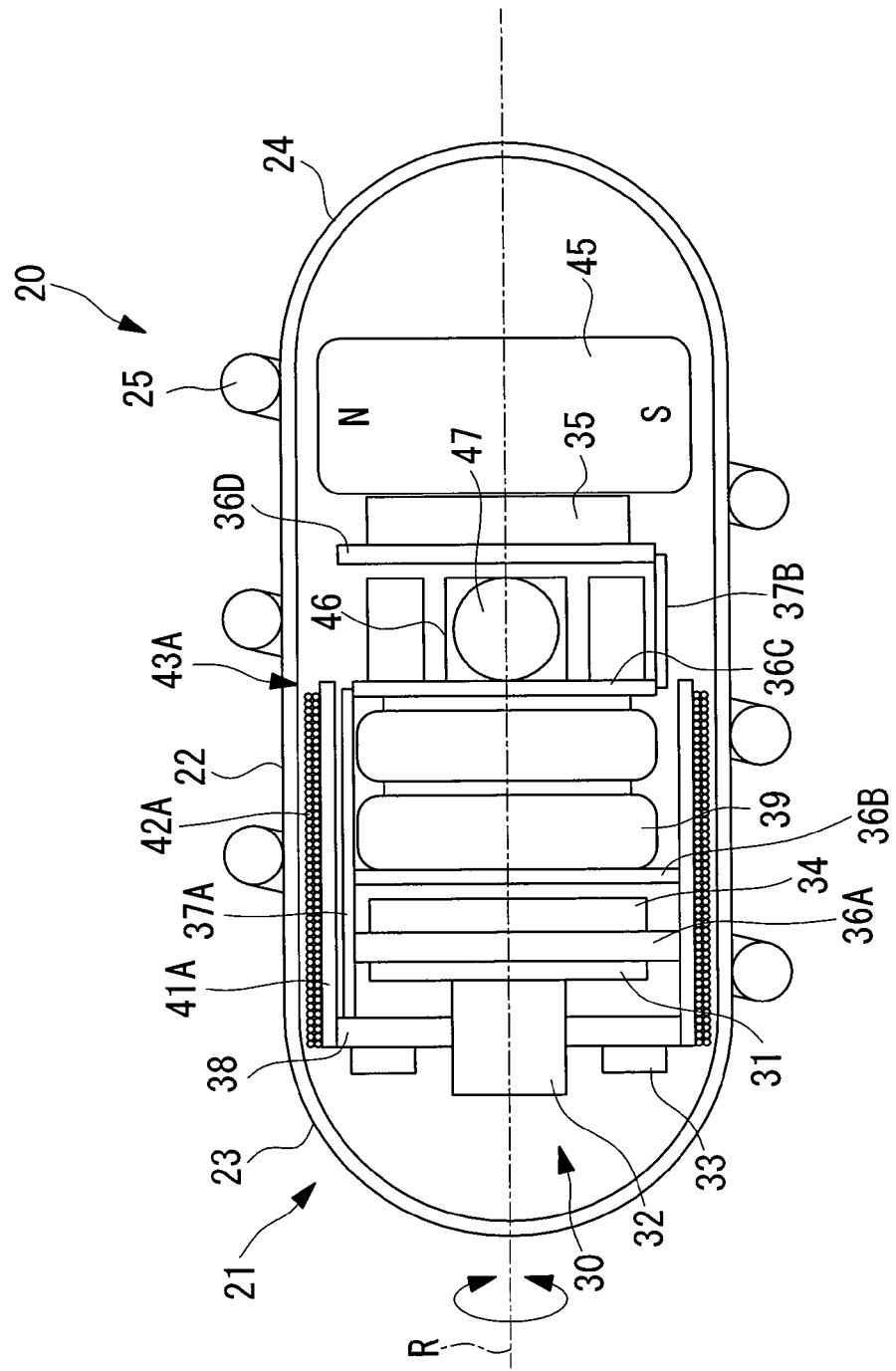
FIG. 16 is a schematic diagram showing a modification of the capsule endoscope of FIG. 11.
Figure 17:
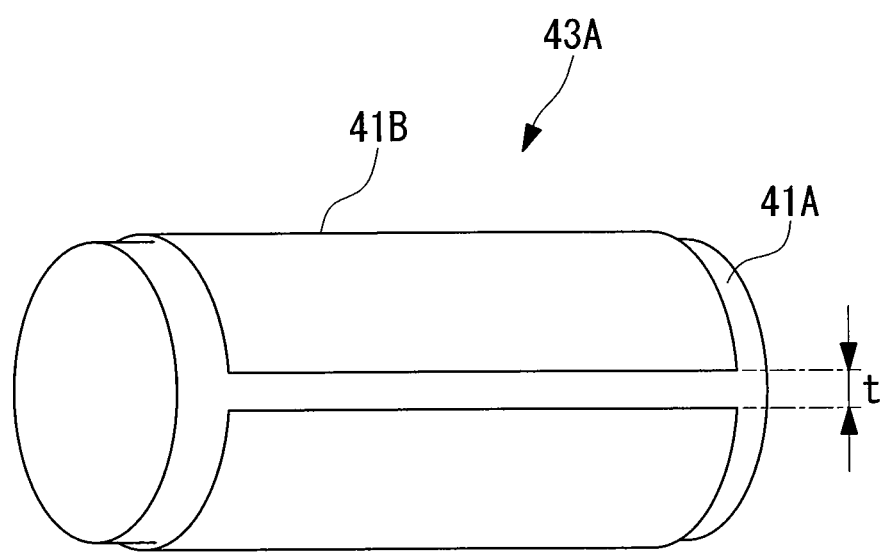
FIG. 17 is a partial perspective view showing the construction of an induction magnetic generator in the capsule endoscope of FIG. 11.

In this embodiment, the capsule endoscope has the structure shown in FIG. 11. However, in place of this structure, the lens group 32, LED 33, the image sensor 31, the signal processor 34, the battery 39, the switching unit 46, the wireless element 35 and the permanent magnet 45 may be disposed in this order from the tip portion 23 side in the outer package 21 of the capsule endoscope 20A as shown in FIGS. 16 and 17. In FIG. 16, the induced magnetism generator 43A is disposed between the outer package 21 and the battery 39, etc., and also disposed so as to cover the elements from the supporting member 38 of LED 33 to the battery 39.

As shown in FIGS. 16 and 17, the induced magnetism generator 43 comprises a cylindrical core member 41A whose center axis is substantially coincident with the rotational axis R, a magnetic induction coil 42A disposed on the outer peripheral portion of the core member 41A, a Permalloy film 41B disposed between the core member 41A and the magnetic induction coil 42A, and a capacitor 42B (not shown) which is electrically connected to the magnetic induction coil 42A and forms the resonance circuit 43.

As shown in FIG. 16, the Permalloy film 41B is formed by designing a magnetic material like sheet film. When the Permalloy film 41B is wound around the core member 41A, a gap t is formed.

As described above, by disposing the Permalloy film 41B between the core member 41A and the magnetic induction coil 42A, the intensity of the alternate magnetic field generated in the induced magnetism generator 43A can be enhanced.

Furthermore, in this embodiment, the resonance frequency and the peak frequency of the resonance circuit 43 are stored in the storage unit 78. In place of this operation, only the resonance frequency may be stored and the peak frequency may be determined from the resonance frequency.

Still furthermore, in this embodiment, an example using the magnetic core 41 as the magnetic induction coil 42A is described. The variation of the characteristic due to the external magnetic field of the magnetic core 41 is one factor of causing the variation of the resonance frequency of the resonance circuit 43. However, there may also occur a phenomenon that the resonance frequency varies likewise when the air core coil is used without using the magnetic core 41. This occurs because the capsule medical device 20 has an electrical circuit and a magnetic material contained in the electrical circuit is affected by an external magnetic field, thereby inducing variation of the resonance frequency of the resonance circuit. In such a case, the same effect could be also achieved if the frequency used in the position detecting system 50 is determined in the frequency setting unit 77 on the basis of the magnetic field angle and the intensity of the external magnetic field M as described with reference to the embodiment. Furthermore, the battery may be considered as the magnetic material in the parts of the capsule endoscope 20.

In this embodiment, the capsule endoscope 20 has the magnet mounted therein and is guided by the external magnetic field. However, even if it is designed so that no magnet is mounted in the capsule endoscope 20, a magnet is mounted in a second capsule endoscope and only the second capsule endoscope is guided, the frequency setting unit 77 can determine the frequency used in the position detecting system 50 on the basis of the resonance frequency of the resonance circuit of the capsule endoscope. Therefore, this embodiment can operate. In this case, the effect that the position of the capsule endoscope can be accurately detected can be likewise obtained. In this case, this system operates as a medical device position detecting system.

Second Embodiment

Next, a capsule endoscope guiding system 100 according to a second embodiment of the present invention will be described with reference to FIGS. 18 and 19.

In the description of this embodiment, the constituent elements common to those of the capsule endoscope guiding system 10 according to the first embodiment described above are represented by the same reference numerals, and the description thereof is omitted.

The basic construction of the capsule endoscope guiding system 100 according to this embodiment is the same as the capsule endoscope guiding system 10 according to the first embodiment, however, it is different in the construction of a resonance circuit 43' and a position detecting system 50' in a capsule endoscope 20'.

FIG. 17 is a diagram showing the capsule endoscope guiding system 100 of this embodiment schematically.

Figure 18:
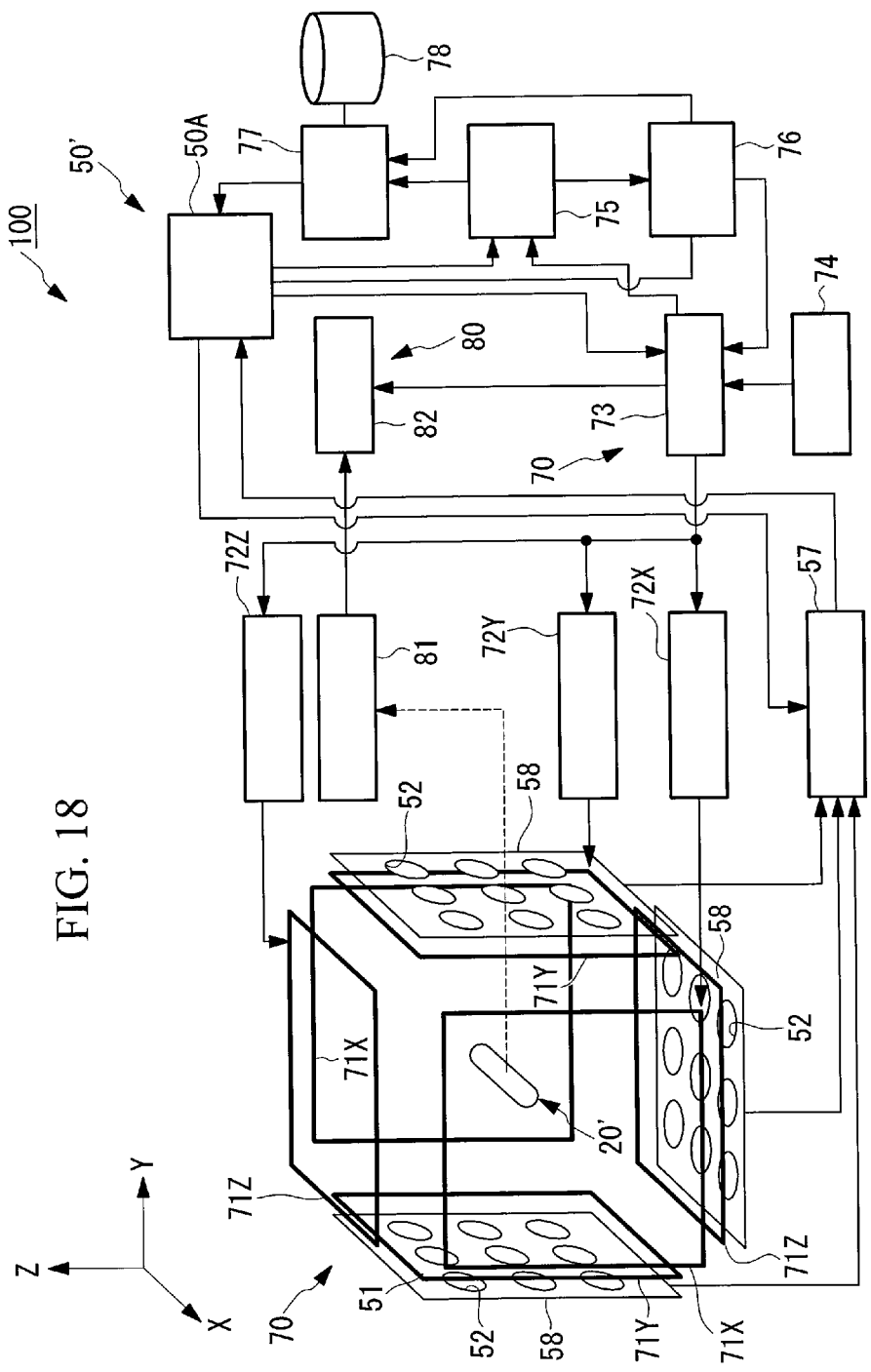
FIG. 18 is a schematic diagram showing a capsule endoscope guiding system according to a second embodiment of the present invention.
Figure 19:
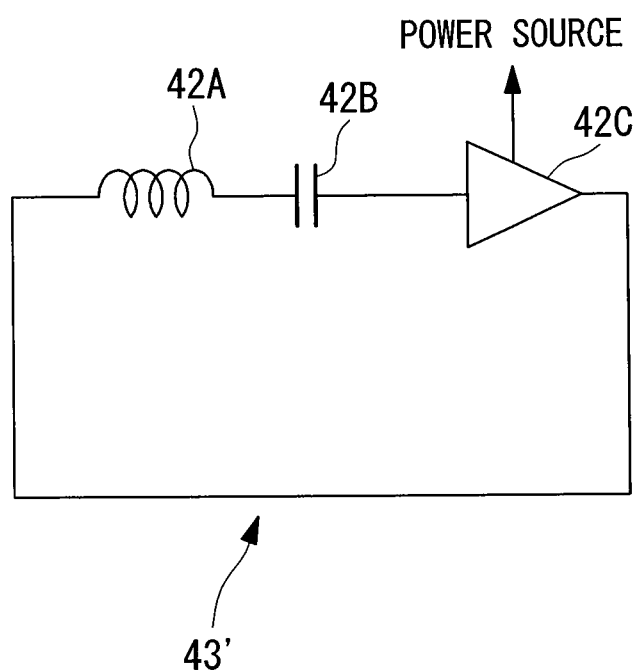
FIG. 19 is a diagram showing a resonance circuit in the capsule endoscope used for the capsule endoscope guiding system of FIG. 18.

In the capsule endoscope guiding system 100 according to this embodiment, the resonance circuit 43' provided in the capsule endoscope 20' constitutes a self-excited oscillation circuit having an amplifier 42C connected to a power source as shown in FIG. 18. Accordingly, in this embodiment, the resonance circuit 43' itself generates an alternate magnetic field at a resonance frequency determined on the basis of the inductance of the magnetic induction coil 42A and the capacitance of the capacitor 42B by using the energy of the power source.

In the capsule endoscope guiding system 100 according to this embodiment, the resonance circuit 43' of the capsule endoscope is constructed by the self-excited oscillation circuit, and thus it is unnecessary that an alternate magnetic field for resonating the resonance circuit 43' is supplied from the outside like the first embodiment. Accordingly, as shown in FIG. 17, the position detecting system 50' is not equipped with the drive coil 51, the signal generating circuit 53, the drive coil driver 54 and the drive coil selector 55 which are connected to the position detecting device 50A.

According to the position detecting system 50' of the capsule endoscope of this embodiment, a pre-stored frequency is read out in accordance with the intensity of the external magnetic field M and the magnetic field angle θ at the position of the capsule endoscope 20', and fed back from the position detecting device 50A to the sense coil reception circuit 57. Therefore, even when the resonance frequency of the self-excited oscillation circuit in the capsule endoscope 20' varies in accordance with the intensity of the external magnetic field M and the magnetic field angle θ, the alternate magnetic field generated by the resonance of the resonance circuit 43' at the resonance frequency after the variation concerned can be detected. Accordingly, the reduction of the detection sensitivity can be prevented. According to the capsule endoscope guiding system 100 having the position detecting system 50' as described above, the position and direction of the capsule endoscope 20' can be detected with high precision, and thus the capsule endoscope 20' can be properly guided without making the operation thereof unstable.

Furthermore, according to this embodiment, the alternate magnetic field generated by the resonance circuit 43' is dependent on the inductance of the magnetic induction coil 42A and the capacitance of the capacitor 42B. Therefore, as compared with the first embodiment, the detection sensitivity is lower, however, the guiding system 100 can be more simply constructed because the drive coils 51, etc. are not required to be provided.

Third Embodiment

Next, a medical device guiding system 110 according to a third embodiment of the present invention will be described with reference to FIGS. 20 to 21.

Figure 20:
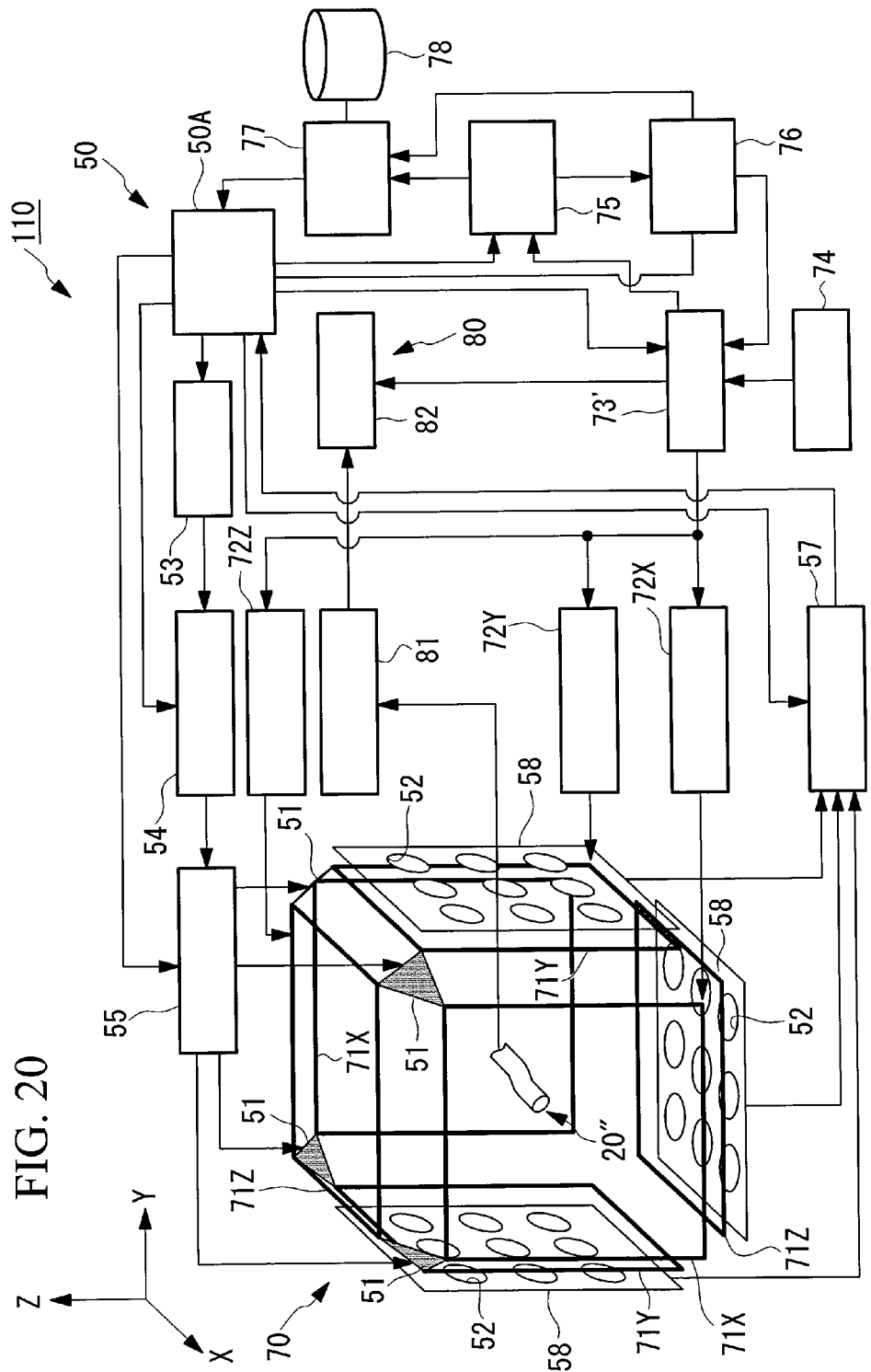
FIG. 20 is a schematic diagram showing a medical device guiding system according to a third embodiment of the present invention.

As shown in FIG. 20, the medical device guiding system 110 according to this embodiment is a system for guiding an endoscope device having a slender insertion portion 20" introduced into a body cavity in place of the capsule endoscope 20 of the capsule endoscope guiding system 10 according to the first embodiment.

Figure 21:
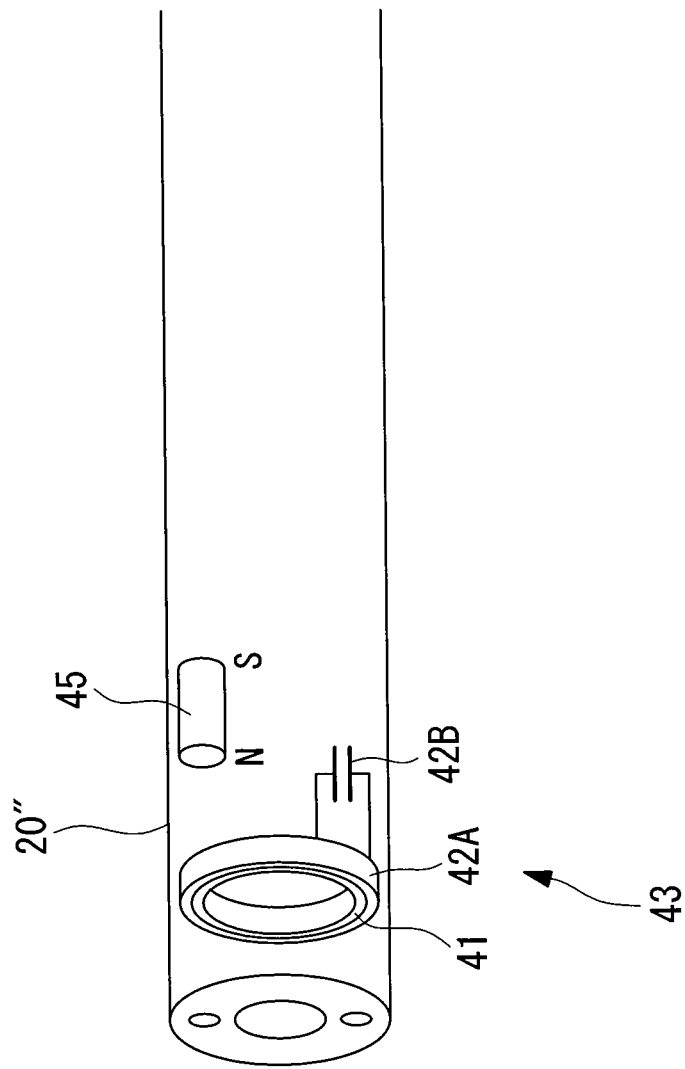
FIG. 21 is schematic diagram showing the structure of the tip of an insertion portion of the endoscope device of the medical device guiding system of FIG. 20.

At the tip of the insertion portion 20" of the endoscope device are arranged the magnetic induction coil 42A and the capacitor 42B constituting the same resonance circuit 43 as the first embodiment and the permanent magnet 45 as shown in FIG. 21. The magnetic core 41 is disposed inside the magnetic induction coil 42A. Furthermore, the permanent magnet 45 is disposed so that the magnetic poles are arranged in a direction along the longitudinal axis of the insertion portion 20".

The medical device guiding system 110 according to this embodiment has substantially the same construction as the guiding system 10 according to the first embodiment. However, it is different in that, instead of the magnetic field control circuit 73, it is provided with a magnetic field control circuit 73' for controlling formation of an external magnetic field M directed in a desired direction on the basis of an input from the input device 74. Image information obtained by the image sensor (not shown) disposed at the tip of the insertion portion 20" is transmitted to the image reception circuit 81 through a cable.

According to the thus-constructed medical device guiding system 110 of this embodiment, when the external magnetic field M directed in a desired direction is generated at the position of the tip of the insertion portion 20" of the endoscope device through the magnetic field control circuit 73' by operating the input device 74, the generated external magnetic field M acts on the permanent magnet 45 disposed at the tip of the insertion portion 20", and the tip of the insertion portion 20" is guided in a direction along the external magnetic field M, whereby the tip of the insertion portion 20" of the endoscope device can be trained in the desired direction.

Furthermore, when the alternate magnetic field is generated at the position of the tip of the insertion portion 20" of the endoscope device through the drive coil 51, the alternate magnetic field acts on the magnetic induction coil 42A disposed at the tip of the insertion portion 20", and the resonance circuit 43 is set to the resonance state, so that a strong alternate magnetic field is generated by the magnetic induction coil 42A. In this case, the frequency characteristic of the magnetic induction coil 42A varies in accordance with the intensity and direction of the external magnetic field M penetrating through the magnetic induction coil 42A. However, according to this embodiment, the alternate magnetic field of the resonance frequency read out on the basis of the intensity of the external magnetic field M and the magnetic field angle θ is generated by the drive coil 51, and also the alternate magnetic field of the read-out peak frequency is detected by the sense coil 52, whereby the position of the tip of the insertion portion 20" can be detected without reducing the detection sensitivity.

In this embodiment, the endoscope device is adopted as the medical device. However, in place of the endoscope device, a catheter may be applied.

Figure 22:
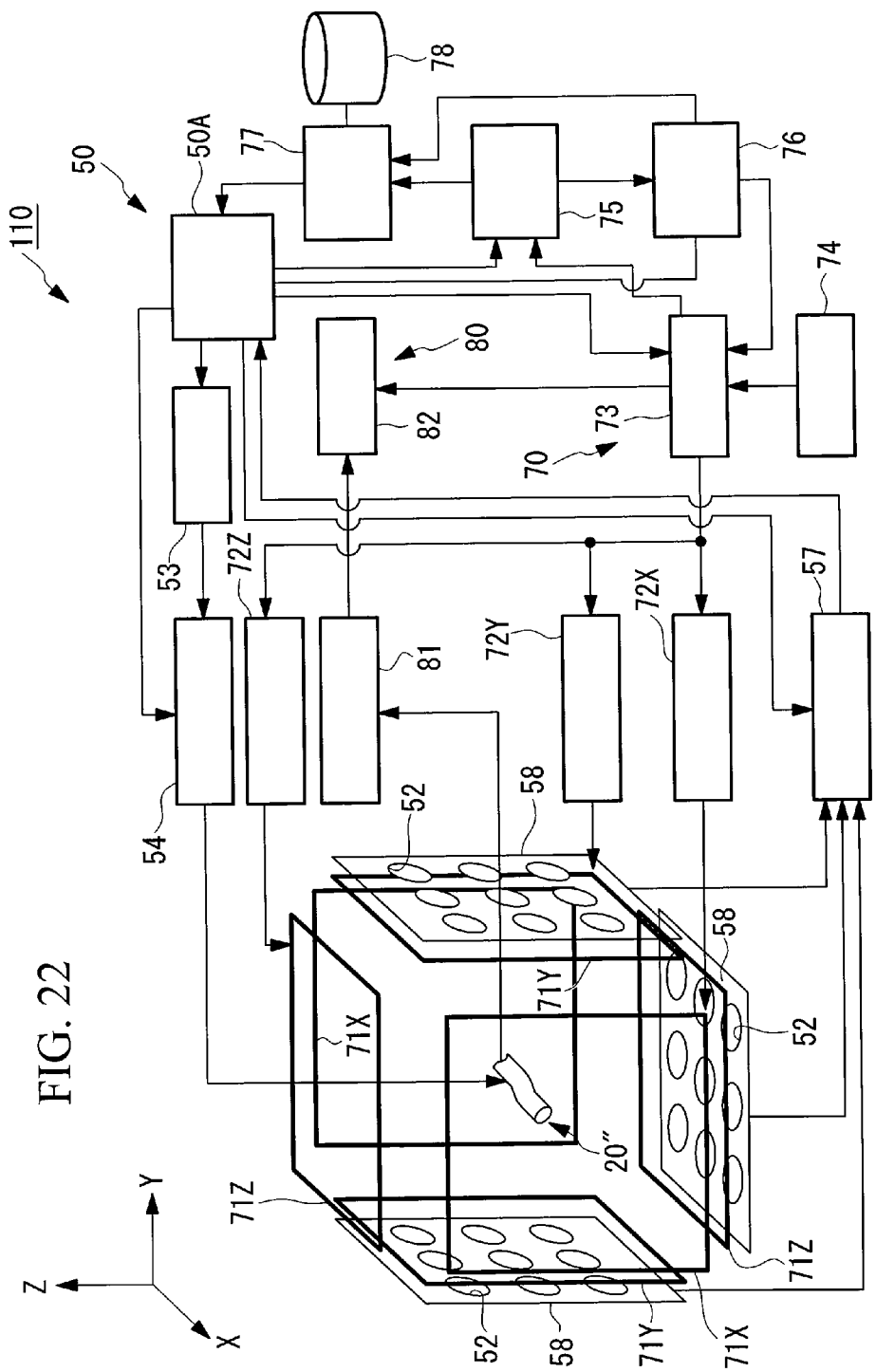
FIG. 22 is a schematic diagram showing a modification of the medical device guiding system of FIG. 20.
Figure 23:
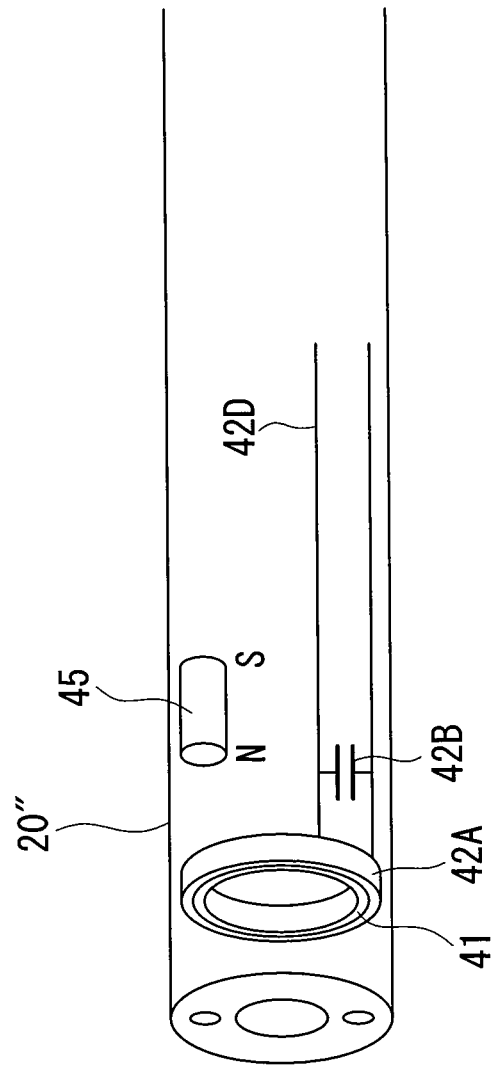
FIG. 23 is a schematic diagram showing the structure of the tip of the insertion portion of the endoscope device of the medical device guiding system of FIG. 22.

Furthermore, in the above embodiment, the closed resonance circuit 43 is disposed at the top of the insertion portion 20" of the endoscope device. In place of this resonance circuit 43, a resonance circuit 43 in which the magnetic induction coil 42A and the capacitor 42B are connected to wires 42D led along the insertion portion 20" in parallel may be adopted as shown in FIGS. 22 and 23. In this case, the drive coil selector 55 and the drive coil 51 are not required. Reference numeral 54' represents a coil driver for driving the resonance circuit 43. The alternate magnetic field of the detection frequency can be surely generated by the resonance circuit 43 disposed at the tip of the insertion portion 20" without relying on the magnetic induction.

Fourth Embodiment

Figure 24:
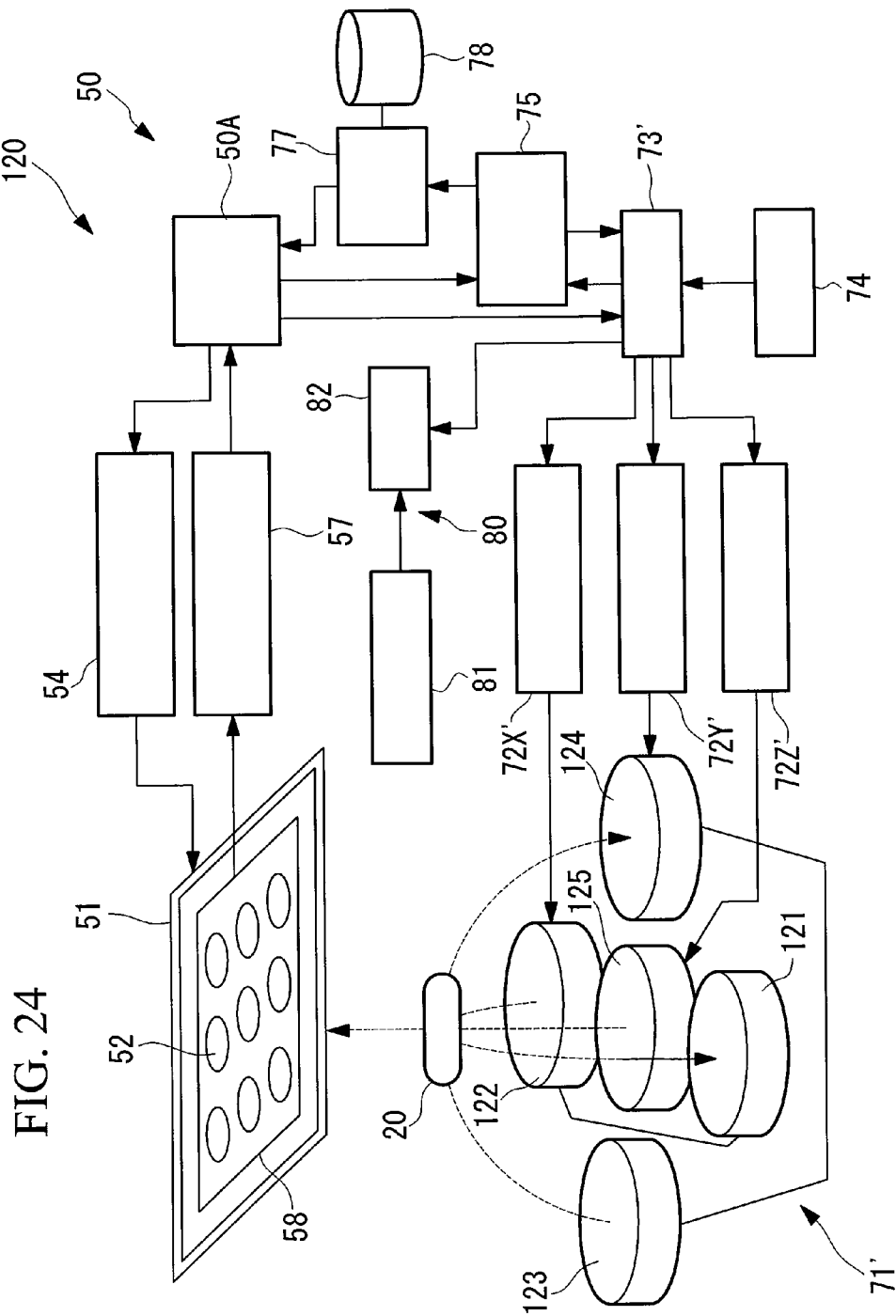
FIG. 24 is a schematic diagram showing a capsule endoscope guiding system according to a fourth embodiment of the present invention.

Next, a capsule endoscope guiding system 120 according to a fourth embodiment of the present invention will be described hereunder with reference to FIG. 24.

In the description of this embodiment, the constituent elements common to those of the capsule endoscope guiding system 10 according to the first embodiment described above are represented by the same reference numerals, and the description thereof is omitted.

The capsule endoscope guiding system 120 according to this embodiment is equipped with a planar type magnetic field generating device 71' comprising plural induction coils 121 to 125 arranged on a plane in place of the magnetic field generating device 71 comprising the Helmholtz coils 71X, 71Y, 71Z. Furthermore, the drive coil 51 and the sense coil 52 are arranged so as to face the induction coils 121 to 125 through the capsule endoscope 20.

According to the thus-constructed capsule endoscope guiding system 120 according to this embodiment, as in the case of the first embodiment, the external magnetic field M having desired intensity and direction can be generated at the position of the capsule endoscope 20 by actuating the planar type magnetic field generating device 71'. The magnetic field generating device 71 comprising the Helmholtz coils 71X, 71Y, 71Z can generate a uniform external magnetic field M at any position in the space S, however, the planar type magnetic field generating device 71' forms a gradient magnetic field (external magnetic field) M whose intensity and direction vary in accordance with the distance from the induction coils 121 to 125.

Accordingly, in the capsule endoscope guiding system 120 according to this embodiment, the resonance circuit 43 is more easily affected by the variation of the frequency characteristic dependently on the position of the capsule endoscope 20 as compared with the first embodiment. However, according to the capsule endoscope guiding system 120 of this embodiment, even when the frequency characteristic of the resonance circuit 43 is varied, the frequency of the alternate magnetic field detected by the sense coil 52 is set to be coincident with the peak frequency. Therefore, the reduction of the detection sensitivity can be prevented, the position of the capsule endoscope 20 can be detected with high precision, and the capsule endoscope 20 can be stably guided in the body cavity.

In the position detecting system 50, 50' of the medical device according to each of the above embodiments, by following the frequency characteristic varying in accordance with the state of the external magnetic field M at all times, the reduction of the detection sensitivity is prevented. In place of this style, the preset detection frequency may be set as a frequency for position detection according to the frequency characteristic as shown in FIG. 25.

Figure 12B:
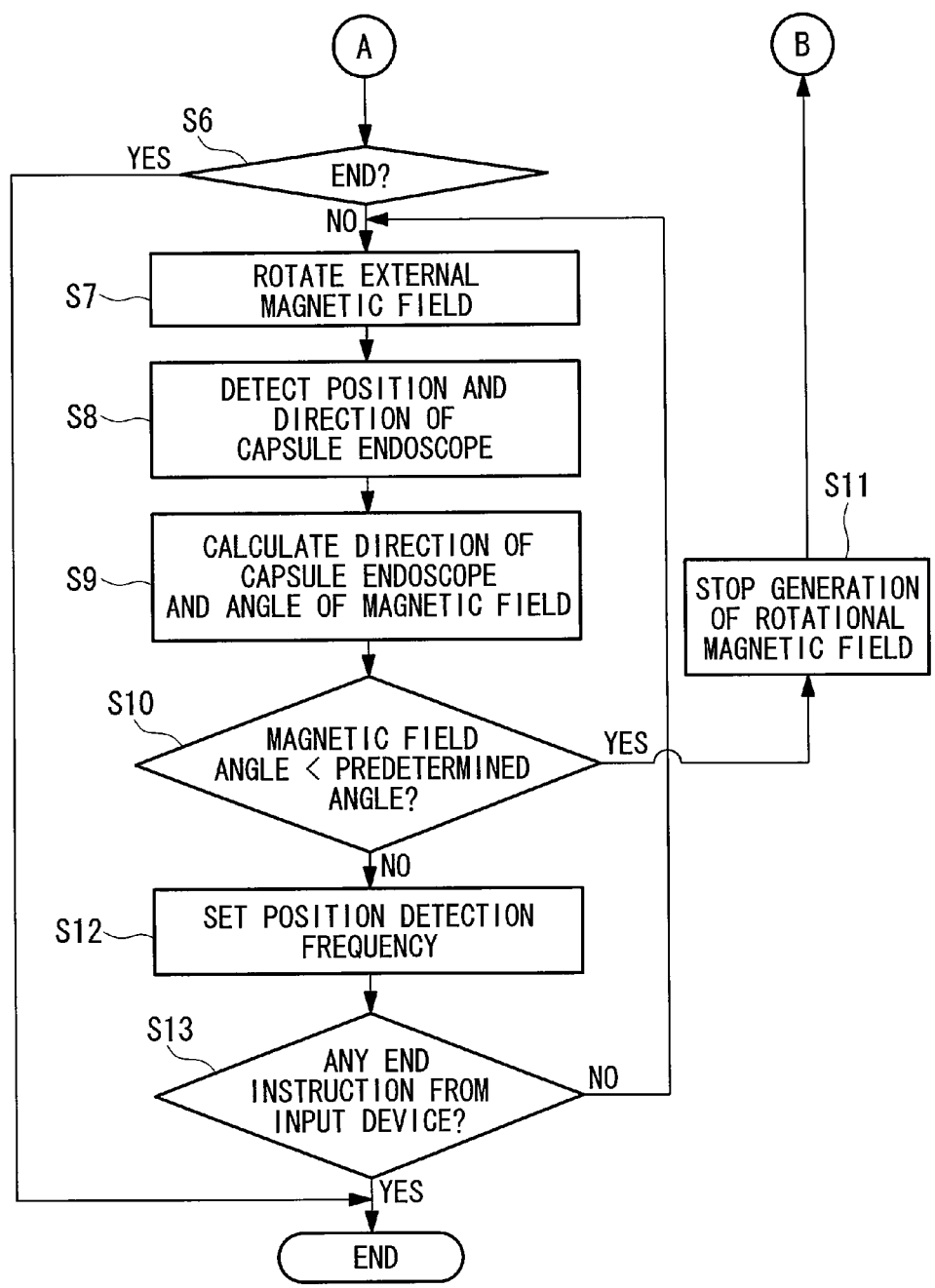
FIG. 12B is a flowchart showing the position detecting method of the capsule endoscope according to the embodiment of the present invention.
Figure 25:
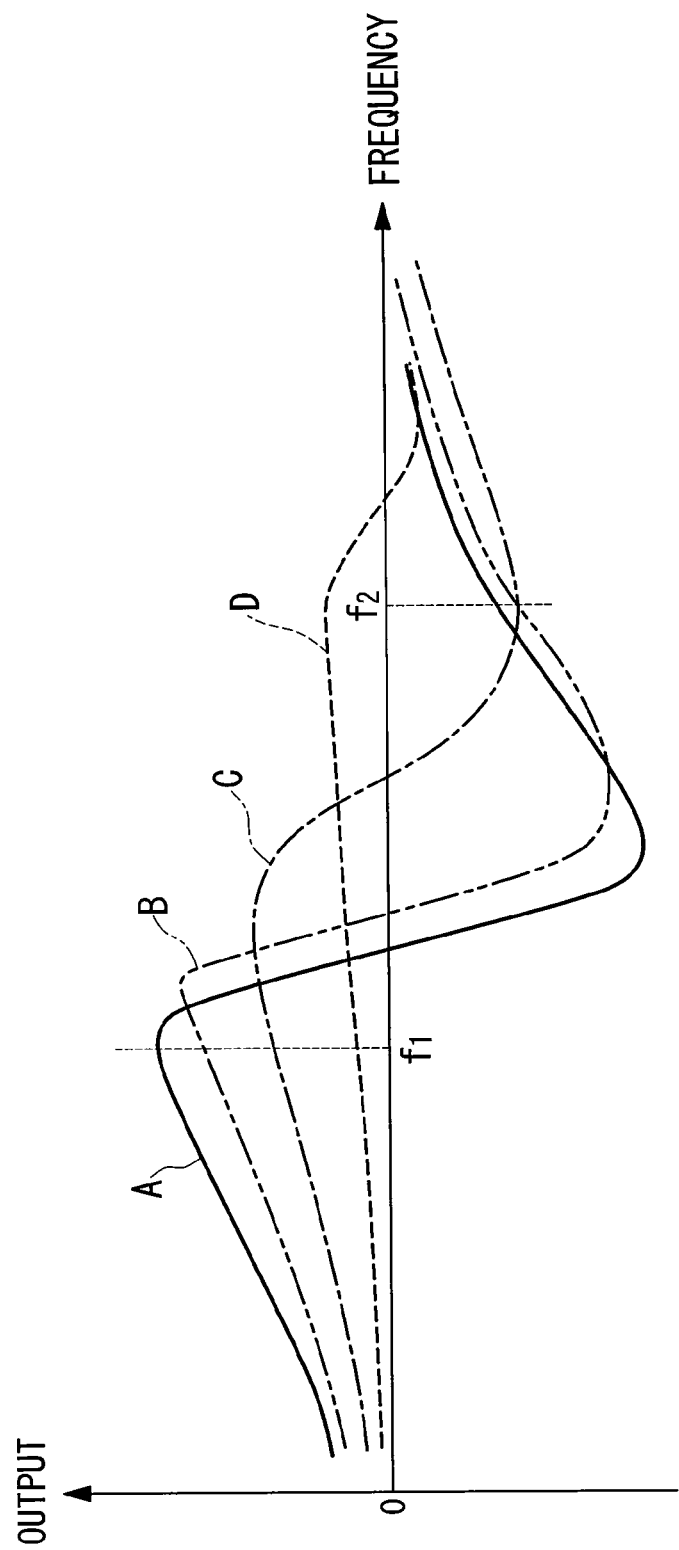
FIG. 25 is a graph showing the frequency characteristic of a resonance circuit of another modification of the present invention.
Figure 26:
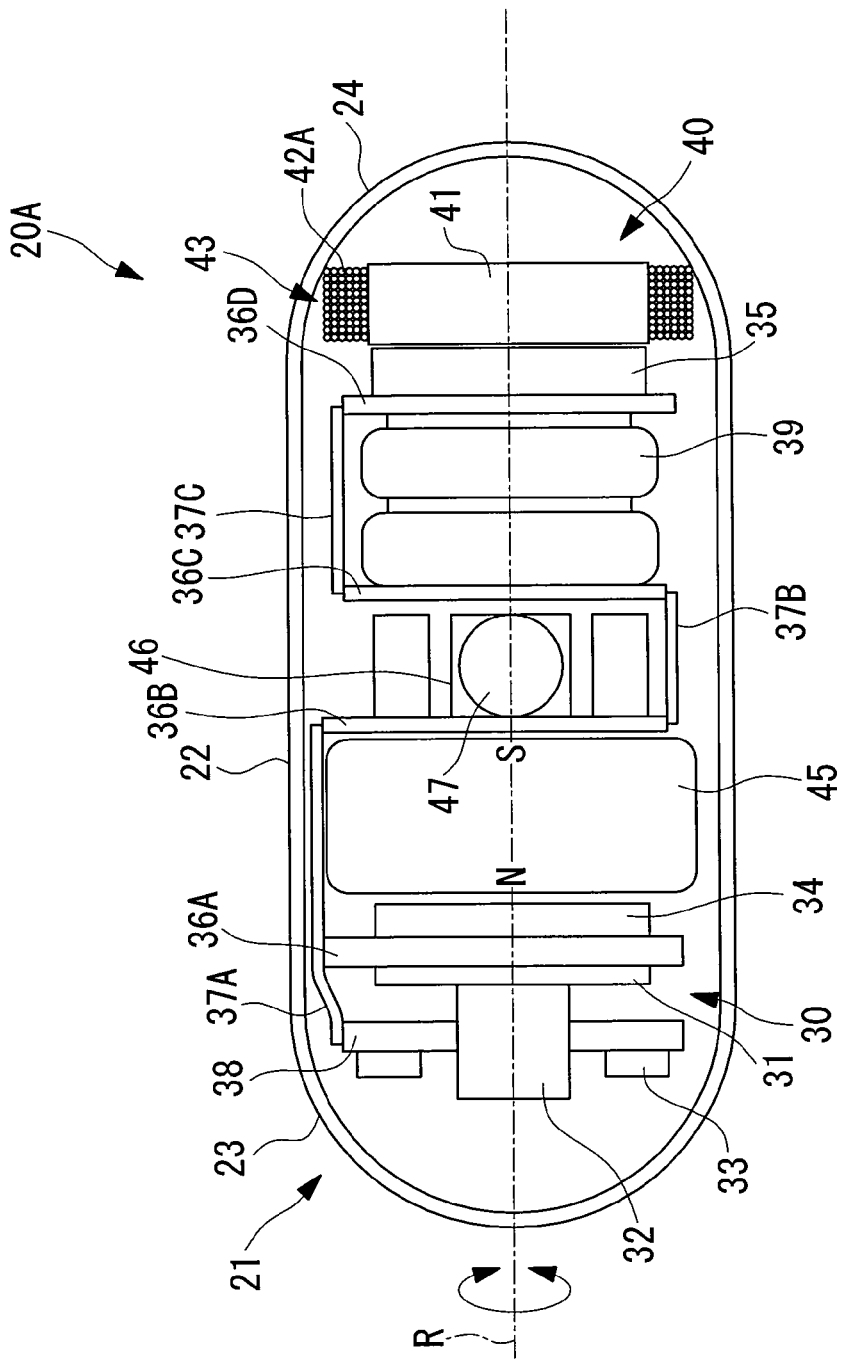
FIG. 26 is a diagram showing another modification of the capsule endoscope used in the capsule endoscope guiding system of the present invention.

That is, as shown in FIG. 25, the frequency characteristic of the resonance circuit 43 when no external magnetic field M acts is represented by A, the frequency characteristic when the external magnetic field M is maximum and the magnetic field angle θ=90° is represented by B, and the frequency characteristic when the external magnetic field M is maximum and the magnetic field angle θ=θa<90° is represented by C. θa represents a predetermined angle for judging stop of occurrence of the external magnetic field M in step S10 of FIG. 12B, for example.

In this case, for example, one of two frequencies at which the output variation of the frequency characteristic A is peak and which is in the neighborhood of the frequency at the low frequency side is set as a first measurement frequency $f_1$, and one of two frequencies at which the output variation of the frequency characteristic C is peak and which is in the neighborhood of the frequency at the high-frequency side is set as a second measurement $f_2$. Accordingly, even when the measurement is not carried out while monitoring the external magnetic field M and varying the frequency for detection, the alternate magnetic field which is generated by the resonance circuit 43 can be relatively stably detected until the magnetic field angle θ is equal to θa. When the resonance frequency is more shifted to the high-frequency side as compared with the condition of the frequency characteristic C (for example, in the case of the frequency characteristic D) the output detected by the sense coil 52 is rapidly lowered, and thus the processing may be made to go to the step S11 of the flowchart of FIG. 12B.

Furthermore, in the above embodiment, the encapsulate endoscope 20, 20' in which the magnetic poles of the permanent magnet 45 are disposed in the direction orthogonal to the longitudinal axis R is used, and the permanent magnet 45 is moved along the rotating external magnetic field M, whereby the capsule endoscope 20, 20' is rotated around the longitudinal axis R. However, in place of this capsule endoscope, a capsule endoscope 20A in which the magnetic poles of the permanent magnet 45 are arranged in the longitudinal axis direction may be adopted. Accordingly, the longitudinal axis R of the capsule endoscope 20A can be moved in the direction along the external magnetic field M, and thus the external magnetic field M can be used to change the direction of the capsule endoscope 20A. In this case, the capsule endoscope 20A is not propelled, and it is committed to the peristaltic motion of a living body or the like.

What is claimed is:

1. A medical device position detecting system which includes a portion configured to be introduced into the body of a subject and guided by an external magnetic field, the system comprising:
a resonance circuit that is mounted in a medical device and contains a magnetic induction coil having a magnetic material inside and wherein the magnetic induction coil generates an alternate magnetic field;
an alternate magnetic field detector that is disposed at the outside of an operation region of the medical device and detects the alternate magnetic field generated by the magnetic induction coil;
a position information, including a position, calculator for calculating position information of the medical device on a basis of the alternate magnetic field detected by the alternate magnetic field detector;
a frequency setting unit including a storage configured to enable setting at least one of frequency of the alternate magnetic field detected by the alternate magnetic field detector and frequency of the alternate magnetic field generated by the magnetic induction coil on a basis of at least one of intensity and direction of the external magnetic field at the position of the magnetic induction coil, said frequency setting unit being physically separate from said resonance circuit.

2. The medical device position detecting system according to claim 1, further comprising an external magnetic field generator for generating the external magnetic field in an operation region of the medical device, and a magnetic field controller for controlling the external magnetic field generating device, wherein the frequency setting unit determines at least one of the intensity and direction of an external magnetic field at the position of the magnetic induction coil on the basis of information from the magnetic field controller, and sets at least one of the frequency of the alternate magnetic field detected by the alternate magnetic field detector and the frequency of the alternate magnetic field generated by the magnetic induction coil.

3. A medical device guiding system comprising the position detecting system according to claim 2, and a magnet that acts on an external magnetic field generated by the external magnetic field generator and is provided to the medical device, wherein the magnetic field controller controls at least one of the position and direction of the medical device.

4. The medical device position detecting system according to claim 1, wherein the frequency setting unit has an external magnetic information calculator for determining at least one of the intensity and direction of the external magnetic field at the position of the magnetic induction coil, and determines at least one of the intensity and direction of an external magnetic field at the position of the magnetic induction coil on the basis of information from the external magnetic field information calculator, and sets at least one of the frequency of the alternate magnetic field detected by the alternate magnetic field detector and the frequency of the alternate magnetic field generated by the magnetic induction coil.

5. The medical device position detecting system according to claim 4, further comprising an external magnetic field generator for generating an external magnetic field in an operation region of the medical device, and a magnetic field controller for controlling the external magnetic field generator, wherein the external magnetic field information calculator determines at least one of the intensity and the direction of the external magnetic field at a position of the magnetic induction coil on the basis of information from the magnetic field controller.

6. A medical device guiding system having the position detecting system according to claim 5 and a magnet that acts on an external magnetic field generated by the external magnetic field generator and is provided to the medical device, at least one of the position and direction of the medical device being controlled by the magnetic field controller, wherein the frequency setting unit sets at least one of the frequency of the alternate magnetic field detected by the alternate magnetic field detecting device and the frequency of the alternate magnetic field generated by the magnetic induction coil on a basis of a composite magnetic field of the magnetic field generated at the position of the magnetic induction coil by the magnet and the external magnetic field generated at the position of the magnetic induction coil by the magnetic field controller.

7. The medical device guiding system according to claim 6, wherein the external magnetic field controller has at least one pair of counter electromagnets which are arranged so as to face each other through an operation region of the medical device, and the electromagnets generate a parallel magnetic field in the operation region of the medical device.

8. The medical device guiding system according to claim 7, wherein there are provided three pairs of counter electromagnets, and the respective counter electromagnets generate magnetic fields in different directions.

9. The medical device guiding system according to claim 6, wherein the magnetic field controller controls rotation of the direction of the external magnetic field.

10. The medical device guiding system according to claim 6, wherein the medical device has a slender insertion portion, and a spiral mechanism that is disposed on an outer peripheral surface of the insertion portion and converts a rotational motion around a longitudinal axis to a propelling motion in the longitudinal axis direction, and the magnet is disposed so that magnetic poles of the magnet are directed in a direction perpendicular to the longitudinal axis.

11. The medical device guiding system according to claim 6, wherein the magnetic field controller controls to stop the external magnetic field when an intersection angle between the direction of the medical device and the direction of the external magnetic field is smaller than a predetermined angle.

12. The medical device guiding system according to claim 6, wherein the external magnetic field generator generates an external magnetic field in any direction, the medical device is equipped with a slender insertion portion, and the magnet is disposed so that magnetic poles of the magnet are directed in a direction along the longitudinal axis of the insertion portion.

13. The medical device guiding system according to claim 6, wherein the magnetic field generator generates a gradient magnetic field.

14. The medical device guiding system according to claim 6, further comprising an external alternate magnetic field generator for generating an external alternate magnetic field in a neighborhood of the frequency set by the frequency setting unit in an operation region of the medical device, wherein the magnetic induction coil receives the external alternate magnetic field and induces the alternate magnetic field.

15. The medical device guiding system according to claim 6, wherein the resonance circuit is driven by an alternate signal in a neighborhood of the frequency set by the frequency setting unit, and the magnetic induction coil generates the alternate magnetic field.

16. The medical device guiding system according to claim 6, wherein the resonance circuit constitutes a self-excited oscillation circuit, and the magnetic induction coil generates the alternate magnetic field.

17. The medical device guiding system according to claim 6, wherein the magnetic material forms a core of the magnetic induction coil.

18. The medical device guiding system according to claim 6, wherein a magnetic material is at least a part of a circuit of the medical device provided in the magnetic induction coil.

19. The medical device guiding system according to claim 6, wherein a magnetic material is in a battery in the circuit.

20. The medical device guiding system according to claim 6, wherein the medical device is any one of a capsule medical device, a catheter, and an endoscope.

21. The medical device position detecting system according to claim 1, wherein the frequency setting unit comprises the storage for storing the position of the medical device in association with the intensity of an external magnetic field generated by the external magnetic field generator and a detection frequency, and sets at least one of the frequency of the alternate magnetic field detected by the alternate magnetic field detector and the frequency of the alternate magnetic field generated by the magnetic induction coil to the detection frequency selected from the storage on the basis of the intensity of the external magnetic field.

22. The medical device position detecting system according to claim 1, wherein the frequency setting unit comprises a magnetic field angle calculator for calculating a magnetic field angle corresponding to an intersection angle between the direction of a external magnetic field at the position of a magnetic induction coil and the direction of the medical device calculated by the position information calculator, and wherein the storage is for storing a magnetic field angle and a detection frequency in association with each other, and at least one of the frequency of the alternate magnetic field detected by the alternate magnetic field detector and the frequency of the alternate magnetic field generated by the magnetic induction coil is set to the detection frequency selected from the storage on the basis of the magnetic field angle.

23. The medical device position detecting system according to claim 1, further comprising an external alternate magnetic field generator for generating an external alternate magnetic field in a neighborhood of the frequency set by the frequency setting unit in an operation region of the medical device, wherein the magnetic induction coil receives the external alternate magnetic field and induces the alternate magnetic field.

24. The medical device position detecting system according to claim 1, wherein the resonance circuit is driven by an alternate signal in a neighborhood of the frequency set by the frequency setting unit, and the magnetic induction coil generates the alternate magnetic field.

25. The medical device position detecting system according to claim 1, wherein the resonance circuit constitutes a self-excited oscillation circuit, and the magnetic induction coil generates the alternate magnetic field.

26. The medical device position detecting system according to claim 1, wherein the magnetic material forms a core of the magnetic induction coil.

27. The medical device position detecting system according to claim 1, wherein the magnetic material is at least a part of a circuit of the medical device provided in the magnetic induction coil.

28. The medical device position detecting system according to claim 27, wherein the magnetic material is in a battery in the circuit.

29. The medical device position detecting system according to claim 1, wherein the medical device is any one of a capsule medical device, a catheter, and an endoscope.

30. A position detecting method for a medical device inserted into the body of a subject, comprising the steps of:
a step of generating an alternate magnetic field from a magnetic induction coil having a magnetic material mounted in the medical device;
a step of detecting the alternate magnetic field generated by the magnetic induction coil disposed at the outside of an operation region of the medical device;
a step of calculating position information containing at least one information of position and direction of the magnetic induction coil on a basis of the alternate magnetic field detected in the step of detecting the alternate magnetic field; and
a step of setting at least one of frequency of the alternate magnetic field detected in the step of detecting the alternate magnetic field and frequency of the alternate magnetic field generated by the magnetic induction coil on a basis of at least one of an intensity and direction of an external magnetic field at the position of the magnetic induction coil, and said setting step being effected using a setting unit that is provided physically separately from said magnetic induction coil.

31. A position detecting method for detecting the position of a medical device when an external magnetic field is made to act on the medical device to guide the medical device, the medical device being inserted in the body of a subject and being equipped with a resonance circuit including a magnetic induction coil and generating an alternate magnetic field signal and with a magnet for guidance, the position detecting method comprises: detecting an alternate magnetic field generated by the magnetic induction coil at the outside of an operation region of the medical device, calculating position information, including a position, of the medical device on a basis of the detected alternate magnetic field, calculating an intensity of an external magnetic field at the position of the medical device on a basis of the calculated position information of the medical device, and setting a frequency of the detected alternate magnetic field on the basis of the calculated intensity of the external magnetic field, said setting step being effected using a setting unit that is provided physically separately from said magnetic induction coil.

* * * * *